(12) United States Patent
Qiu

(10) Patent No.: US 11,500,417 B2
(45) Date of Patent: Nov. 15, 2022

(54) ELECTRONIC CIGARETTE CONTROL METHOD, ELECTRONIC CIGARETTE, AND WEARABLE ELECTRONIC DEVICE

(71) Applicant: JOYETECH EUROPE HOLDING GMBH, Zug (CH)

(72) Inventor: Wei-Hua Qiu, ChangZhou (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 541 days.

(21) Appl. No.: 16/535,207

(22) Filed: Aug. 8, 2019

(65) Prior Publication Data
US 2019/0357598 A1 Nov. 28, 2019

Related U.S. Application Data

(63) Continuation-in-part of application No. PCT/CN2017/079353, filed on Apr. 1, 2017.

(51) Int. Cl.
| | |
|---|---|
| *A24F 47/00* | (2020.01) |
| *A61B 5/11* | (2006.01) |
| *A63F 13/825* | (2014.01) |
| *G06F 1/16* | (2006.01) |
| *A63F 13/212* | (2014.01) |
| *H04W 4/029* | (2018.01) |
| *A24F 40/50* | (2020.01) |
| *A24F 40/60* | (2020.01) |
| *A24F 40/65* | (2020.01) |
| *A24F 40/10* | (2020.01) |

(52) U.S. Cl.
CPC .............. *G06F 1/163* (2013.01); *A24F 40/50* (2020.01); *A24F 40/60* (2020.01); *A24F 40/65* (2020.01); *A61B 5/1118* (2013.01); *A63F 13/212* (2014.09); *A63F 13/825* (2014.09); *H04W 4/029* (2018.02); *A24F 40/10* (2020.01)

(58) Field of Classification Search
None
See application file for complete search history.

(56) References Cited

U.S. PATENT DOCUMENTS

| | | | |
|---|---|---|---|
| 11,000,076 B2 * | 5/2021 | Tremblay | A24F 40/60 |
| 2013/0340775 A1 * | 12/2013 | Juster | A24F 40/53 |
| | | | 131/273 |

(Continued)

FOREIGN PATENT DOCUMENTS

| | | | | |
|---|---|---|---|---|
| CA | 2876267 A1 * | 6/2015 | ............. | A24F 40/53 |
| CA | 3056499 A1 * | 9/2018 | ........... | A24B 15/167 |

(Continued)

*Primary Examiner* — Chico A Foxx
(74) *Attorney, Agent, or Firm* — ScienBiziP, P.C.

(57) ABSTRACT

An electronic cigarette and a wearable electronic device which can function together or separately are disclosed. The electronic cigarette includes a communication interface, a controller, a heat generator, and a power supply. The wearable electronic device includes a sensor, a controller, and a communication interface. The electronic cigarette and the wearable electronic device can cooperatively work. Data can be exchanged between the electronic cigarette and the wearable electronic device and each can process the received data, thereby controlling the electronic cigarette to operate in certain manners. The electronic cigarette can function with greater intelligence and with more diversity.

20 Claims, 18 Drawing Sheets

(56) References Cited

U.S. PATENT DOCUMENTS

| | | | | |
|---|---|---|---|---|
| 2014/0305450 A1* | 10/2014 | Xiang | ............... | A24F 40/65 |
| | | | | 700/266 |
| 2014/0366897 A1* | 12/2014 | Liu | ............... | A24F 40/60 |
| | | | | 131/329 |
| 2015/0181945 A1* | 7/2015 | Tremblay | ............... | A24F 40/53 |
| | | | | 131/328 |
| 2015/0371529 A1* | 12/2015 | Dolecki | ............... | G06F 1/1694 |
| | | | | 700/94 |
| 2017/0208867 A1* | 7/2017 | Li | ............... | G08C 17/02 |
| 2017/0325507 A1* | 11/2017 | Xiang | ............... | F22B 1/284 |
| 2018/0263283 A1* | 9/2018 | Popplewell | ............... | A24B 15/167 |
| 2018/0289074 A1* | 10/2018 | Tremblay | ............... | A24F 40/65 |
| 2019/0158938 A1* | 5/2019 | Bowen | ............... | A61M 15/06 |
| 2020/0008481 A1* | 1/2020 | Tremblay | ............... | A24F 40/65 |
| 2021/0112877 A1* | 4/2021 | Tremblay | ............... | A24F 40/53 |
| 2021/0315278 A1* | 10/2021 | Fraser | ............... | A24F 40/57 |
| 2021/0360981 A1* | 11/2021 | Memari | ............... | A24F 40/50 |
| 2022/0061396 A1* | 3/2022 | Lord | ............... | A24F 40/50 |

FOREIGN PATENT DOCUMENTS

| | | | | |
|---|---|---|---|---|
| CA | 2996380 C * | 8/2020 | ............ | A24F 40/65 |
| CN | 205103959 U * | 3/2016 | | |
| CN | 205624477 U | 10/2016 | | |
| CN | 106174705 A | 12/2016 | | |
| EP | 3085256 A1 * | 10/2016 | ............ | A24F 40/30 |
| EP | 3680735 A1 * | 7/2020 | ............ | A24F 40/53 |
| WO | WO-2015076515 A1 * | 5/2015 | ............ | A24F 47/008 |
| WO | WO-2018146453 A1 * | 8/2018 | ............ | A24B 15/167 |

\* cited by examiner

US 11,500,417 B2

ELECTRONIC CIGARETTE CONTROL METHOD, ELECTRONIC CIGARETTE, AND WEARABLE ELECTRONIC DEVICE

CROSS-REFERENCE TO RELATED APPLICATIONS

This application is a continuation-in-part under 35 U.S.C. § 120 of international patent application PCT/CN2017/079353 filed Apr. 1, 2017.

FIELD

The subject matter relates to smoking simulations, and more particularly, to an electronic cigarette control method, an electronic cigarette, and a wearable electronic device.

BACKGROUND

Electronic cigarettes can simulate the feeling of tobacco smoking. The electronic cigarette usually includes an atomizer and a battery. The atomizer includes a heat generator and a storage container for storing an aerosol-forming material. When driven by the battery, the heat generator heats the aerosol-forming material to generate smoke that the user can inhale. However, the existing electronic cigarette lacks diversity in function, and is not intelligent enough to satisfy the diverse needs of user. On the other hand, wearable electronic devices, which are more diversified in function, have developed. The wearable electronic device can be used as an independent device, and also be an accessory of other electronic devices. The wearable electronic device can be worn around the human body to monitor at least a state of the body. Thus, when the electronic cigarette cooperates with the wearable electronic device, the electronic cigarette may become more intelligent and more diversified in function to improve the user experience.

BRIEF DESCRIPTION OF THE DRAWINGS

Implementations of the present technology will now be described, by way of example only, with reference to the attached figures.

DETAILED DESCRIPTION

Figure 1:
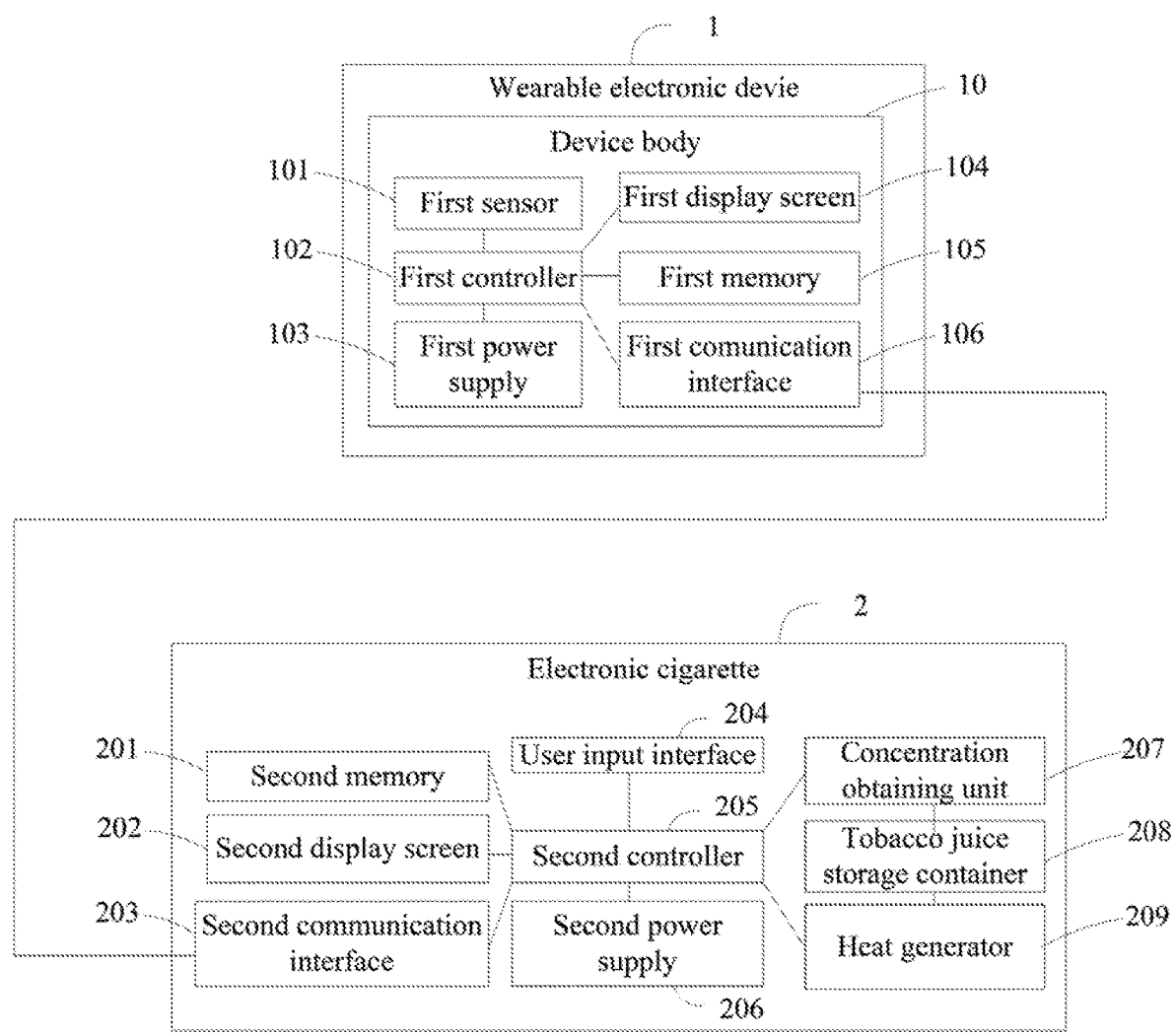
FIG. 1 is a block diagram illustrating a first embodiment of an electronic cigarette control system including an electronic cigarette and a wearable electronic device.

It will be appreciated that for simplicity and clarity of illustration, where appropriate, reference numerals have been repeated among the different figures to indicate corresponding or analogous components. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

FIG. 1 illustrates a first embodiment of an electronic cigarette control system 100 including a wearable electronic device 1 and an electronic cigarette 2. The wearable electronic device 1 includes a device body 10 and a connecting element 4 (shown in FIG. 17). The device body 10 can be affixed to and removed from the connecting element 4. The wearable electronic device 1, such as a smart bracelet, a smart watch, a smart ring, can be worn on the human body.

The device body 10 includes a first communication interface 106. The electronic cigarette 2 includes a second communication interface 203. The first communication interface 106 and the second communication interface 203 can establish data connection between each other for data communication. The first communication interface 106 and the second communication interface 203 can establish wired connection. For example, one of the first communication interface 106 and the second communication interface 203 is a plug, and the other one is a jack. Thus, the first communication interface 106 can be inserted into the second communication interface 203 to achieve wired connection. For example, the first communication interface 106 is a USB plug, and the second communication interface 203 is a USB jack. The first communication interface 106 and the second communication interface 203 can also establish wireless connection, such as connection by at least one of cellular network, WI-FI, infrared, BLUETOOTH, ZIGBEE, and NFC.

The device body 10 further includes a first sensor 101, a first controller 102, and a first power supply 103. The first controller 102 is electrically connected to the first sensor 101, the first power supply 103, and the second communication interface 203.

The first sensor 101 senses a body state of the user to obtain data accordingly (hereinafter, "body state data", labeled as: $D_0$).

The first sensor 101 can include at least one of an accelerometer, an optical heart rate monitor, a skin electric reaction sensor, a bioelectrical impedance sensor, and a pulse wave sensor. The sensed body state data $D_0$ includes at least one of a number of steps taken by the user, a heart rate, a perspiration rate, and a pulse of the user. The accelerometer can record the number of steps taken by the user. The optical heart rate monitor can monitor the heart rate of the user. The skin electric reaction sensor can sense the perspiration rate of the user. The bioelectrical impedance sensor can monitor the blood flow based on the inherent impedance of the biological body, and transfer the sensed blood flowrate to the heart rate, the respiration rate, and the skin electrical reaction index. The pulse wave sensor can sense the pulse of the user.

The first controller 102 controls the first communication interface 106 and the second communication interface 203 to establish data connection with each other, and controls the first communication interface 106 to transmit the sensed body state data $D_0$ of the user to the second communication interface 203.

The first power supply 103 supplies electric power to the device body 10.

In an embodiment, the device body 10 further includes a first display screen 104 that is electrically connected to the first controller 102. The first display screen 104 displays working information of the wearable electronic device 1. The working information of the wearable electronic device 1 includes the sensed body state data $D_0$ of the user. The working information of the wearable electronic device 1 further includes a remaining voltage of the first power supply 103, a current time, a current date, and a current operating mode of the wearable electronic device 1. The device 10 can further includes a first memory 105.

In an embodiment, the electronic cigarette 2 further includes a second memory 201, a second controller 205, a second power supply 206, and a heat generator 209. The second controller 205 is electrically connected to the second memory 201, the second communication interface 203, the second power supply 206, and the heat generator 209.

The second memory 201 stores a relationship between body state data of the user and health levels, and a relationship between the health levels and first smoking parameters.

The second communication interface 203 receives the sensed body state data $D_0$ of the user from the first communication interface 106.

The second power supply 206 supplies electric power to the electronic cigarette 2.

The heat generator 209 heats the aerosol-forming material to generate smoke that the user can inhale.

The second controller 205 obtains the sensed body state data $D_0$ of the user from the second communication interface 203, determines a health level L of the user according to the sensed body state data $D_0$ of the user and the relationship between the body state data of the user and the health levels stored in the second memory 201. The second controller 205 further determines a first smoking parameter (labeled as: $D_1$) according to the determined health level L of the user and the relationship between the health levels and the first smoking parameters stored in the second memory 201. The second controller 205 controls the electric power supplied to the heat generator 209 by the second power supply 206 according to the determined first smoking parameter $D_1$.

The stored health levels are classified according to the state of health of the human body.

The first smoking parameter $D_1$ can be set according to at least one of a manufacturer of the electronic cigarette 2, a health caring platform, a doctor, and a family member. The first smoking parameter $D_1$ includes a time for smoking, a duration for smoking, a number of inhalations when smoking, and working temperature/working voltage/working power of the heat generator 209. Since nicotine can excite the body, sleep quality may be affected when the user smokes late at night. Thus, the time for smoking needs to be adjusted according to the body state data $D_0$ of the user. In addition, the amount of nicotine that user inhales increases when the duration for smoking and/or the number of inhalations when smoking increases. Furthermore, the working temperature/working voltage/working power of the heat generator 209 affect the amount of smoke to be inhaled per inhalation, thereby affecting the amount of nicotine that user takes in. Thus, the duration for smoking and the number of inhalations when smoking, and the working temperature/working voltage/working power of the heat generator 209 also need to be adjusted according to sensed body state data $D_0$ of the user.

When the first smoking parameter $D_1$ includes at least one of the time for smoking, the duration for smoking, and the number of inhalations when smoking, the first smoking parameter $D_1$ can be the time for smoking, the duration for smoking, and the number of inhalations when smoking within a preset time period. For example, the first smoking parameter $D_1$ can include limiting the number of inhalations when smoking, for example, the first smoking parameter $D_1$ can be 50 smoke inhalations in the next 24 hours.

The aerosol-forming material can be one of tobacco juice, prepared opium paste, and pipe tobacco.

For example, the body state data $D_0$ of the user is the number of steps taken by the user (labeled as $N_1$). The health levels include four levels: excellent, good, moderate, and bad. The first smoking parameter $D_1$ is the number of inhalations when smoking. The relationship between the body state data of the user and health levels is that when $0 \leq N_1 < 5000$, the corresponding health level is bad. When $5000 \leq N_1 < 10000$, the corresponding health level is moderate. When $10000 \leq N_1 < 15000$, the corresponding health level is good. When $N_1 \geq 15000$, the corresponding health level is excellent. The relationship between the health levels and first smoking parameters is that when the health level is bad, the number of smoke inhalations equals to 10. When the health level is moderate, the number of inhalations when smoking equals to 50. When the health level is good, the number of inhalations when smoking equals to 80. When the health level is excellent, the number of inhalations when smoking equals to 100.

The second controller 205 controls the electric power supplied to the heat generator 209 by the second power supply 206 according to the determined first smoking parameter $D_1$, specifically, when the first smoking parameter $D_1$ includes the time for smoking, the second controller 205 controls the time when the second power supply 206 and the heat generator 209 are connected to or disconnected from each other. For example, the time can be 8:00 am to 8:00 pm within a single day. The second controller 205 can connect the second power supply 206 to the heat generator 209 during the time, but disconnect the second power supply 206 from the heat generator 209 during the remaining time. When the second power supply 206 and the heat generator 209 are disconnected, even if the user lights the electronic cigarette 2, the heat generator 209 does not generate heat. When the first smoking parameter $D_1$ includes the duration or the number of inhalations when smoking, the second controller 205 calculates the total duration or the total number of inhalations when smoking within the preset time period. When the calculated total duration reaches a preset duration or the calculated total inhalations reach a preset number of inhalations, the second controller 205 disconnects the second power supply 206 from the heat generator 209 within the preset time period. When the first smoking parameter $D_1$ includes the working temperature of the heat generator 209, the second controller 205 controls the voltage or the power which the second power supply 206 outputs to the heat generator 209 and maintain the actual temperature of the heat generator 209 at the working temperature. When the first smoking parameter $D_1$ includes the working voltage or the working power of the heat generator 209, the second controller 205 maintains the voltage which the second power supply 206 outputs to the heat generator 209 at the working voltage, or maintains the power which the second power supply 206 outputs to the heat generator 209 at the working power.

In an embodiment, the electronic cigarette 2 further includes a second display device 202 that is electrically connected to the second controller 205. The second display device 202 displays operation indications and working information of the electronic cigarette 2. The working information of the electronic cigarette 2 includes the sensed body state data $D_0$ of the user from the second communication interface 203, the determined health level L of the user, and the determined first smoking parameter $D_1$. The working information of the electronic cigarette 2 further includes a remaining voltage of the second power supply 206, a current operating mode of the electronic cigarette 2, and a current smoking parameter.

In an embodiment, the electronic cigarette 2 further includes a user input interface 204 that is electrically connected to the second controller 205. The user input interface 204 is for the user to input control signals for selecting the operating mode of the electronic cigarette 2. The electronic cigarette 2 includes a manual mode and an automatic mode. The user can select one operating mode through the user input interface 204. When the electronic cigarette 2 is in the manual mode, the electronic cigarette 2 operates according to a second smoking parameter (labeled as: $D_2$) that are input by the user through the user input interface 204. When the electronic cigarette 2 is in the automatic mode, the electronic cigarette 2 operates according to the first smoking parameter $D_1$ calculated by the second controller 205. The second smoking parameter $D_2$ represents desired smoking parameter of the user input to the user input interface 204.

The second smoking parameter $D_2$ includes the time for smoking, the duration for smoking, the number of inhalations when smoking, and working temperature/working voltage/working power of the heat generator 209. The second controller 205 controls the electric power supplied to the heat generator 209 by the second power supply 206 according to the second smoking parameter $D_2$, specifically, when the second smoking parameter $D_2$ includes the time for smoking, the second controller 205 controls time when the second power supply 206 and the heat generator 209 are connected or disconnected. For example, the time can be 8:00 am to 8:00 pm within a single day. The second controller 205 can connect the second power supply 206 to the heat generator 209 during that time, but disconnect the second power supply 206 from the heat generator 209 for the remaining time. When the second power supply 206 and the heat generator 209 are disconnected, even if the user lights the electronic cigarette 2, the heat generator 209 does not generate heat. When the second smoking parameter $D_2$ includes the duration for smoking or the number of inhalations when smoking, the second controller 205 calculates the total duration for smoking or the total number of inhalations when smoking within the preset time period. When the calculated total duration reaches a preset duration or the calculated total inhalations reach a preset number of inhalations, the second controller 205 disconnects the second power supply 206 from the heat generator 209 within the preset time period. When the second smoking parameter $D_2$ includes the working temperature of the heat generator 209, the second controller 205 controls the voltage or the power that the second power supply 206 outputs to the heat generator 209 and maintain the actual temperature of the heat generator 209 at the working temperature. When the second smoking parameter $D_2$ includes the working voltage or the working power of the heat generator 209, the second controller 205 maintains the voltage that the second power supply 206 outputs to the heat generator 209 at the working voltage, or maintains the power which the second power supply 206 outputs to the heat generator 209 at the working power.

In an embodiment, the second memory 201 further stores an upper threshold $D_U$ and a lower threshold $D_L$. When the user selects the manual mode and inputs the second smoking parameter $D_2$ to the user input interface 204, the second controller 205 compares the input second smoking parameter $D_2$ with the upper threshold $D_U$ and the lower threshold $D_L$. When the input second smoking parameter $D_2$ is greater than or equals to the lower threshold $D_L$ and less than or equals to the upper threshold $D_U$, the second controller 205 controls the heat generator 209 to operate normally. That is, the second power supply 206 is electrically connected to the heat generator 209 and supplies electric power to the heat generator 209 according to the second smoking parameter $D_2$. When the input second smoking parameter $D_2$ is less than the lower threshold $D_L$ or greater than the upper threshold $D_U$, the second controller 205 locks out the heat generator 209. That is, the second power supply 206 is disconnected from the heat generator 209. Furthermore, the electronic cigarette 2 displays a first warning signal on the second display device 202 for reminding the user that the input smoking parameter is out of range. Thus, damage to the human body and/or the electronic cigarette 2 can be prevented in case the user randomly inputs the second smoking parameter $D_2$ under the manual mode. One example of locking out the heat generator 209 may be that the second power supply 206 does not supply power to the heat generator 209 (that is, the heat generator 209 does not generate heat) even when the user lights the electronic cigarette 2.

In other embodiments, the electronic cigarette 2 can output the first warning signal to the user through another warning device, such as an indication lamp, a vibrator, or a speaker.

In an embodiment, the aerosol-forming material of the electronic cigarette 2 is tobacco juice. The electronic cigarette 2 further includes a tobacco juice storage container 208 for storing the tobacco juice. The heat generator 209 communicates with the tobacco juice storage container 208, and can heat the tobacco juice in tobacco juice storage container 208. The second memory 201 further stores a relationship between health levels and first concentrations of nicotine. The second controller 205 further determines a first concentration of nicotine (labeled as: $C_0$) according to the relationship between health levels L and first concentrations of nicotine. The working information of the electronic cigarette 2 displayed by the second display device 202 further includes the determined first concentration of nicotine $C_0$. Thus, the user can add nicotine in the tobacco juice storage container 208, so as to achieve a concentration that equals to or is less than the determined first concentration. The first concentrations of nicotine match the health levels of the user. The first concentrations of nicotine can be set according to at least one of the manufacturer of the electronic cigarette, the health caring platform, the doctor, and the family member.

In an embodiment, the electronic cigarette 2 further includes a concentration obtaining unit 207 that is electrically connected to the second controller 205. The concentration obtaining unit 207 can be a concentration sensor. At least a portion of the concentration obtaining unit 207 is inserted into the tobacco juice storage container 208 to sense a concentration of nicotine (labeled as: $C_1$) in the tobacco juice. The second controller 205 obtains the sensed concentration of nicotine $C_1$ from the concentration obtaining unit 207, and compares the sensed concentration of nicotine $C_1$ with the determined first concentration of nicotine $C_0$. When the sensed concentration of nicotine $C_1$ is greater than the determined first concentration of nicotine $C_0$, the second controller 205 locks out the heat generator 209. That is, the second power supply 206 is disconnected from the heat generator 209. Furthermore, the electronic cigarette 2 displays a second warning signal on the second display device 202 for reminding the user of a high level of concentration of nicotine. When the sensed concentration of nicotine $C_1$ is less than or equals to the determined first concentration of nicotine $C_0$, the second controller 205 unlocks the heat generator 209. That is, the second power supply 206 is connected to the heat generator 209 and supplies electric power to the heat generator 209 according to the first smoking parameter $D_1$ or the second smoking parameter $D_2$. The concentration obtaining unit 207 can sense a pH value of the tobacco juice to obtain the concentration of nicotine $C_1$. In another embodiment, the concentration obtaining unit 207 can also directly sense the concentration of nicotine $C_1$. In other embodiments, each time the tobacco juice is added into the tobacco juice storage container 208, the user can input the concentration of nicotine $C_1$ of the added tobacco juice. After the electronic cigarette 2 receives the input concentration of nicotine $C_1$, the electronic cigarette 2 stores the input concentration of nicotine $C_1$ in the second memory 201. Thus, the concentration obtaining unit 207 can directly obtain the input concentration of nicotine $C_1$ in the second memory 201, that is, the concentration obtaining device 207 does not need to be inserted into the tobacco juice storage container 208.

In other embodiments, the electronic cigarette 2 can output the second warning signal to the user through another warning device, such as an indication lamp, a vibrator, or a speaker.

In other embodiments, the added target element is not limited to nicotine, but also can be flavours, liquid medicine, ethanediol, or propanetriol. The concentration obtaining unit 207 obtains the first concentration of the target element (labeled as: $C_0'$). The second memory 201 stores a relationship between health levels and first concentrations of the target element. The second controller 205 determines a first concentration of the target element $C_0'$ according to the relationship between health levels and first concentrations of the target element, compares the sensed concentration of the target element with the determined first concentration of the target element $C_0'$, and locks out or unlocks the heat generator 209 accordingly. Taking the target element as liquid medicine for example, a too high or too low concentration of liquid medicine is not useful to the user. Thus, the second controller 205 compares the sensed concentration of liquid medicine with the determined first concentration of liquid medicine. When the sensed concentration of liquid medicine is greater than or less than the determined first concentration of liquid medicine, the second controller 205 locks out the heat generator 209. When the sensed concentration of liquid medicine equals to the determined first concentration of liquid medicine, the second controller 205 unlocks the heat generator 209. The first concentrations of the target element match the health levels of the user. The first concentrations can be set according to at least one of the manufacturer of the electronic cigarette, the health caring platform, doctor, and a family member.

In another embodiment, the memory 105 stores a relationship between the body state data of the user and health levels. The first controller 102 determines a health level L of the user according to the sensed body state data $D_0$ of the user and the relationship between the body state data of the user and health levels stored in the first memory 101. The first controller 102 then controls the first communication interface 106 to transmit the determined health level L of the user to the second communication interface 203. The second memory 201 stores a relationship between the health levels and first smoking parameters. The second controller 205 obtains the determined health level L of the user from the second communication interface 203, and determines a first smoking parameter $D_1$ according to the determined health level L of the user and the relationship between the health levels and first smoking parameters stored in the second memory 201. The second controller 205 controls the electric power supplied to the heat generator 209 by the second power supply 206 according to the determined first smoking parameter $D_1$.

In yet another embodiment, the memory 105 stores a relationship between the body state data of the user and health levels, and a relationship between the health levels and first smoking parameters. The first controller 102 determines a health level L of the user according to the sensed body state data $D_0$ of the user and the relationship between the body state data of the user and health levels stored in the first memory 101, and determines a first smoking parameter $D_1$ according to the determined health level L of the user and the relationship between the health levels and first smoking parameters. The first controller 102 then controls the first communication interface 106 to transmit the determined first smoking parameter $D_1$ to the second communication interface 203. The second controller 205 obtains the determined first smoking parameter $D_1$ from the second communication interface 203, and controls the electric power supplied to the heat generator 209 by the second power supply 206 according to the first smoking parameter $D_1$.

In yet another embodiment, the first communication interface 103 and the second communication interface 203 are connected to each other through a third-party device (not shown). The first communication interface 103 can transmit the sensed body state data $D_0$ of the user to the third-party device. The third-party device then transmits the sensed body state data $D_0$ of the user to the second communication interface 203. The third-party device can be one of a mobile terminal (such as cell phone), a server, and a personal computer.

Since the third-party device has data processing and analyzing capabilities, the relationship between the body state data of the user and health levels can also be stored in the third-party device. When the third-party device receives the sensed body state data $D_0$ of the user from the first communication interface 103, the third-party device can determine a health level L of the user according to the relationship between the body state data of the user and health levels, and transmit the determined health level L of the user to the second communication interface 203. The second memory 201 stores a relationship between the health levels and the first smoking parameters. The second controller 205 obtains the determined health level L of the user from the second communication interface 203, and determines a first smoking parameter $D_1$ according to the determined health level L of the user and the relationship between the health levels and first smoking parameters stored in the second memory 201. The second controller 205 controls the electric power supplied to the heat generator 209 by the second power supply 206 according to the determined first smoking parameter $D_1$.

In yet another embodiment, the relationship between the body state data of the user and the health levels, and the relationship between the health levels and the first smoking parameters can both be stored in the third-party device. When the third-party device receives the sensed body state data $D_0$ of the user from the first communication interface 103, the third-party device determines a health level L of the user according to the sensed body state data $D_0$ of the user and the relationship between the body state data of the user and the health levels, and determines a first smoking parameter $D_1$ according to the determined health level L of the user and the relationship between the health levels and the first smoking parameters. The third-party device transmits the determined first smoking parameter $D_1$ to the second communication interface 203. The second controller 205 obtains the determined first smoking parameter $D_1$ to the second controller 205, and controls the electric power supplied to the heat generator 209 by the second power supply 206 according to the determined first smoking parameter $D_1$.

In other embodiments, the first concentration of the target element $C_0'$ can also be determined and transmitted by the wearable electronic device 1 or the third-party device.

Figure 2:
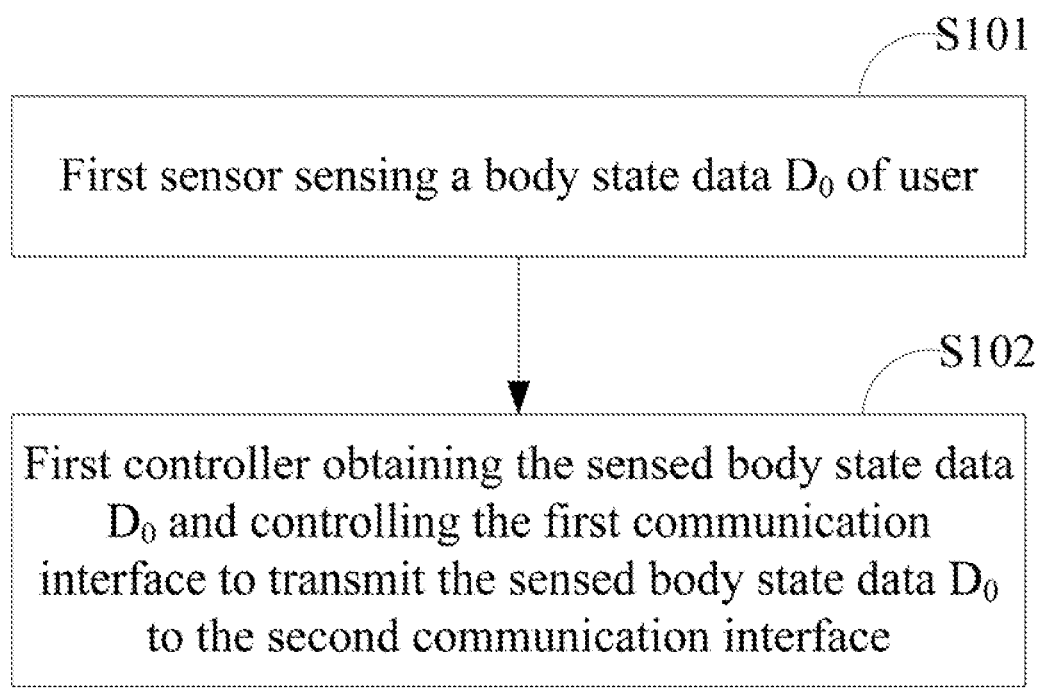
FIG. 2 is a flowchart illustrating an embodiment of an electronic cigarette control method executed by the wearable electronic device of FIG. 1.

FIG. 2 illustrates an electronic cigarette control method executed by the electronic cigarette control system 100 including the wearable electronic device 1 and the electronic cigarette 2. The electronic cigarette control method includes a submethod executed by the wearable electronic device 1 and a submethod executed by the electronic cigarette. The submethod executed by the wearable electronic device 1 begins at step S101.

At step S101, the first sensor 101 senses the body state of the user to obtain data $D_0$ accordingly (hereinafter, "body state data"). Then, the procedure goes to step S102.

At step S102, the first controller 102 controls the first communication interface 106 and the second communication interface 203 to establish data connection with each other, and controls the first communication interface 106 to transmit the sensed body state data $D_0$ of the user to the second communication interface 203.

Figure 3:
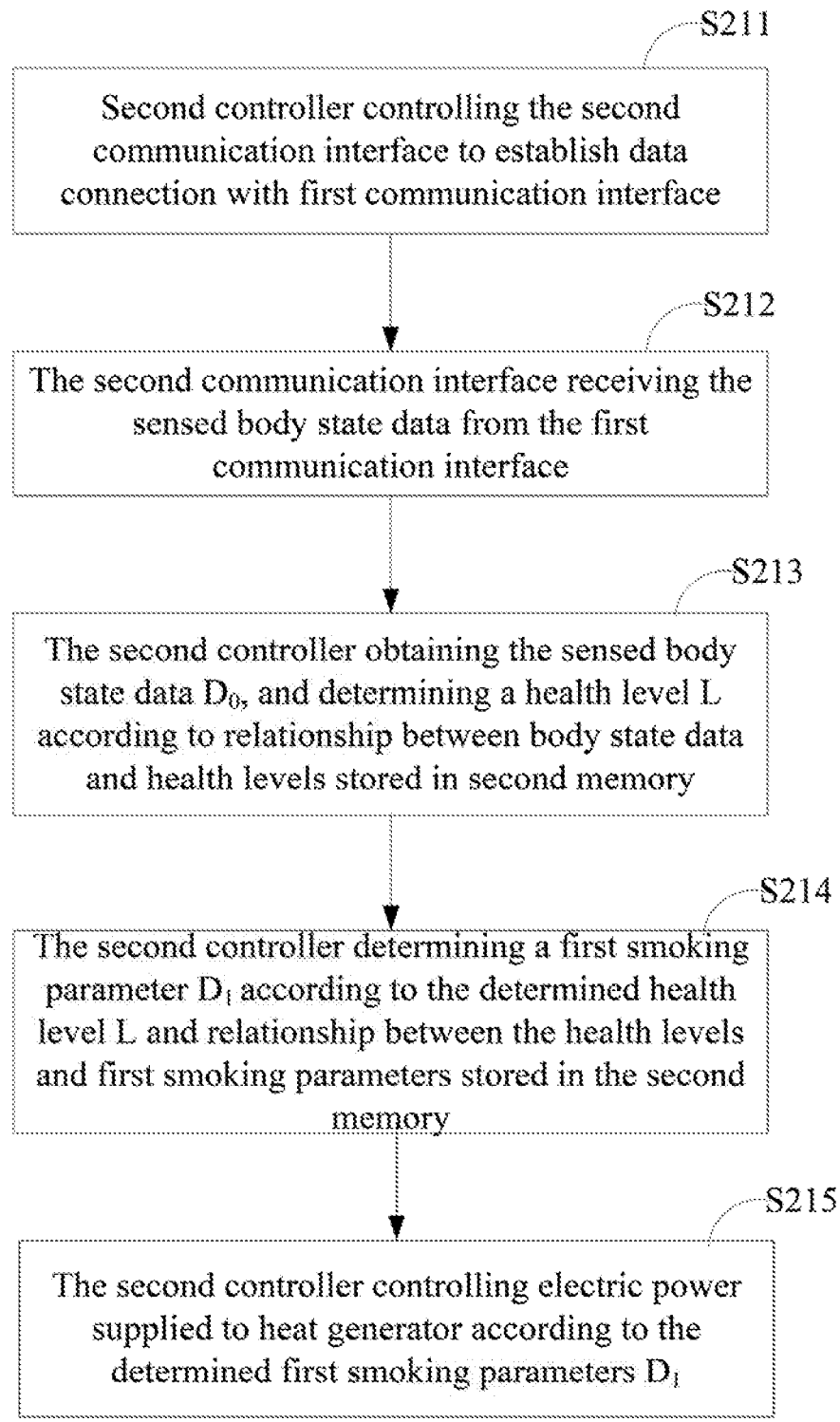
FIG. 3 is a flowchart illustrating an electronic cigarette control method executed by the electronic cigarette of FIG. 1, in a first embodiment.

Then, the electronic cigarette 2 can analyze the sensed body state data $D_0$ of the user, and control the heat generator 209 of the electronic cigarette 2 to operate accordingly. Referring to FIG. 3, the submethod of a first embodiment executed by the electronic cigarette 2 begins at step S211.

At step S211, the second communication interface 203 establishes data connection with the first communication interface 106. Then, the procedure goes to step S212.

At step S212, the second communication interface 203 receives the sensed body state data $D_0$ of the user from the first communication interface 106. Then, the procedure goes to step S213.

At step S213, the second controller 205 obtains the sensed body state data $D_0$ of the user from the second communication interface 203, and determines a health level L of the user according to the sensed body state data $D_0$ of the user and the relationship between body state data of the user and health levels stored in the second memory 201. Then, the procedure goes to step S214.

At step S214, the second controller 205 determines a first smoking parameter $D_1$ according to the determined health level L of the user and the relationship between the health levels and first smoking parameters stored in the second memory 201. Then, the procedure goes to step S215.

At step S215, the second controller 205 controls the electric power supplied to the heat generator 209 by the second power supply 206 according to the determined first smoking parameter $D_1$.

Figure 4:
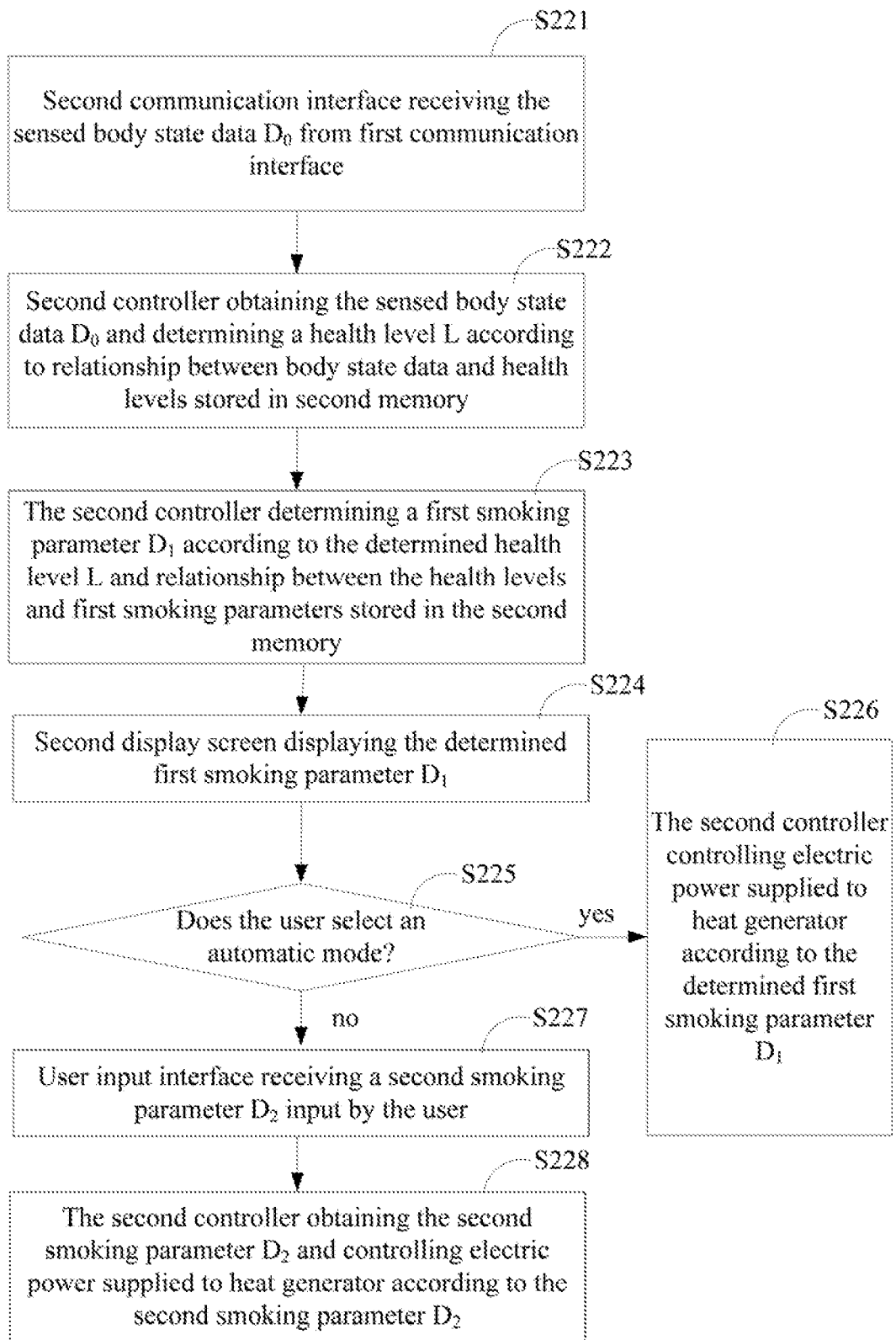
FIG. 4 is a flowchart illustrating an electronic cigarette control method executed by the electronic cigarette of FIG. 1, in a second embodiment.

Referring to FIG. 4, the submethod of a second embodiment executed by the electronic cigarette 2 begins at step S221.

At step S221, the second communication interface 203 receives the sensed body state data $D_0$ of the user from the first communication interface 106. Then, the procedure goes to step S222.

At step S222, the second controller 205 obtains the sensed body state data $D_0$ of the user from the second communication interface 203, and determines a health level L of the user according to the sensed body state data $D_0$ of the user and the relationship between body state data of the user and health levels stored in the second memory 201. Then, the procedure goes to step S223.

At step S223, the second controller 205 determines a first smoking parameter $D_1$ according to the determined health level L of the user and the relationship between the health levels and first smoking parameters stored in the second memory 201. Then, the procedure goes to step S224.

At step S224, the second display device 202 displays the determined first smoking parameter $D_1$. Then, the procedure goes to step S225.

At step S225, the second controller 205 controls the electronic cigarette 2 to enter an automatic or a manual mode according to a selection of the user. If the automatic mode is selected, the electronic cigarette 2 enters the automatic mode, and the procedure goes to step S226. Otherwise, if the automatic mode is not selected, the electronic cigarette 2 enters the manual mode, and the procedure goes to step S227.

The electronic cigarette 3 can display the user input interface 204 for the user to select the operating mode of the electronic cigarette 2. The user input interface 204 includes a first option corresponding to the automatic mode and a second option corresponding to the manual mode. When the first option is selected, the electronic cigarette 2 determines that the user is selecting the automatic mode. When the second option is selected, the electronic cigarette 2 determines that the user selects the manual mode. In actual use, when neither the first option nor the second option is selected in a preset time period, the electronic cigarette 2 enters a default operating mode. The default operating mode can be either one of the automatic mode and the manual mode.

In other embodiments, the illustrated order of the step S225 can be changed, for example, the step S225 can be executed before any previous step. Furthermore, when the electronic cigarette 2 enters the manual mode, the above steps S221~S224 are omitted to reduce execution complexity.

At step S226, the second controller 205 controls the electric power supplied to the heat generator 209 by the second power supply 206 according to the determined first smoking parameter $D_1$.

At step S227, the user input interface 204 receives a second smoking parameter $D_2$ input by the user. Then, the procedure goes to S228.

At step S228, the second controller 205 obtains the second smoking parameter $D_2$ from the user input interface 204, and controls the electric power supplied to the heat generator 209 by the second power supply 206 according to the second smoking parameter $D_2$.

Figure 5:
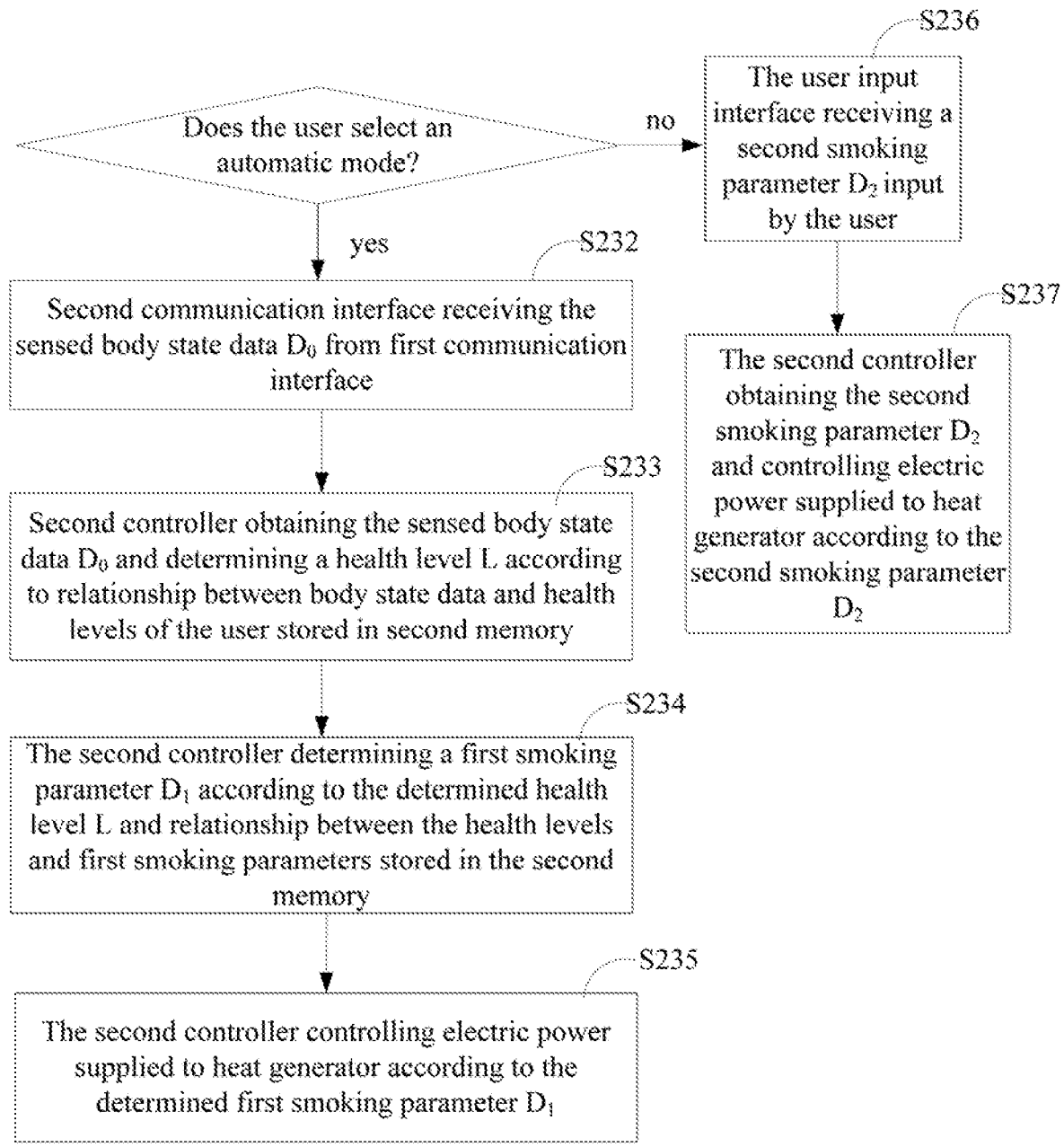
FIG. 5 is a flowchart illustrating an electronic cigarette control method executed by the electronic cigarette of FIG. 1, in a third embodiment.

FIG. 5 illustrates that the submethod of a third embodiment executed by the electronic cigarette 2 begins at step S231.

At step S231, the second controller 205 controls the electronic cigarette 2 to enter the automatic or the manual mode according to a selection of the user. When the automatic mode is selected, the electronic cigarette 2 enters the automatic mode, and the procedure goes to step S232; otherwise, when the automatic mode is not selected, the electronic cigarette 2 enters the manual mode, and the procedure goes to step S236.

At step S232, the second communication interface 203 receives the sensed body state data $D_0$ of the user from the first communication interface 106. Then, the procedure goes to step S233.

At step S233, the second controller 205 obtains the sensed body state data $D_0$ of the user from the second communication interface 203, and determines a health level L of the user according to the sensed body state data $D_0$ of the user and the relationship between body state data of the user and health levels stored in the first memory 201. Then, the procedure goes to step S234.

At step S234, the second controller 205 determines a first smoking parameter $D_1$ according to the determined health level L of the user and the relationship between the health levels and first smoking parameters stored in the second memory 201. Then, the procedure goes to step S235.

At step S235, the second controller 205 controls the electric power supplied to the heat generator 209 by the second power supply 206 according to the determined first smoking parameter $D_1$.

At step S236, the user input interface 204 receives a second smoking parameter $D_2$ input by the user. Then, the procedure goes to step S237.

At step S237, the second controller 205 obtains the second smoking parameter $D_2$ from the user input interface 204, and controls the electric power supplied to the heat generator 209 by the second power supply 206 according to the second smoking parameter $D_2$.

Compared to the submethod of the first embodiment, the user can select the automatic mode for the electronic cigarette 2 in the submethod of the second and third embodiments, to allow flexibility in using the electronic cigarette 2. In addition, the second display screen 202 in the second embodiment can display the determined first smoking parameter $D_1$, to allow the user to evaluate the determined first smoking parameter $D_1$ and determine whether to switch to the manual mode. In the third embodiment, the electronic cigarette 2 can first determine whether the user selects the automatic mode. When the automatic mode is not selected, the electronic cigarette 2 stops communication with the first communication interface 106, and stops the determination of the health level L and the first smoking parameter $D_1$. The submethods executed by the electronic cigarette 2 are simplified to save electric power.

Figure 6:
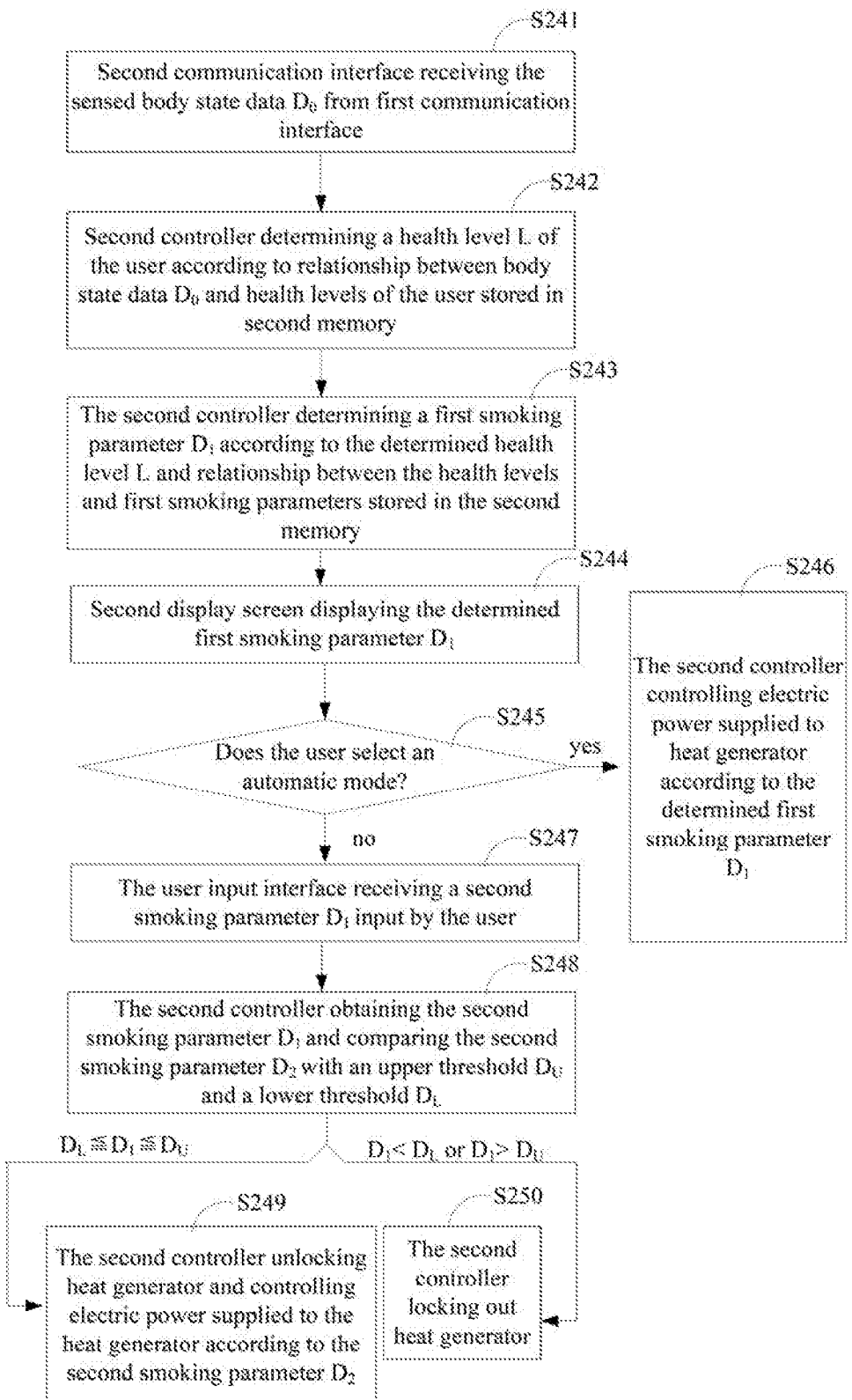
FIG. 6 is a flowchart illustrating an electronic cigarette control method executed by the electronic cigarette of FIG. 1, in a fourth embodiment.

FIG. 6 illustrates the submethod in a fourth embodiment executed by the electronic cigarette 2, which begins at step S241.

At step S241, the second communication interface 203 receives the sensed body state data $D_0$ of the user from the first communication interface 106. Then, the procedure goes to step S242.

At step S242, the second controller 205 obtains the sensed body state data $D_0$ of the user from the second communication interface 203, and determines a health level L of the user according to the sensed body state data $D_0$ of the user and the relationship between body state data of the user and health levels stored in the second memory 201. Then, the procedure goes to step S243.

At step S243, the second controller 205 determines a first smoking parameter $D_1$ according to the determined health level L of the user and the relationship between the health levels and first smoking parameters stored in the second memory 201. Then, the procedure goes to step S244.

At step S244, the second display screen 202 displays the determined first smoking parameter $D_1$.

At step S245, the second controller 205 controls the electronic cigarette 2 to enter the automatic or the manual mode according to a selection of the user. When the automatic mode is selected, the electronic cigarette 2 enters the automatic mode, and the procedure goes to step S246. Otherwise, when the automatic mode is not selected, the electronic cigarette 2 enters the manual mode, and the procedure goes to step S247.

At step S246, the second controller 205 controls the electric power supplied to the heat generator 209 by the second power supply 206 according to the determined first smoking parameter $D_1$.

At step S247, the user input interface 204 receives a second smoking parameter $D_2$ input by the user. Then, the procedure goes to step S248.

At step S248, the second controller 205 obtains the second smoking parameter $D_2$ from the user input interface 204, and compares the second smoking parameter $D_2$ with the upper threshold $D_U$ and the lower threshold $D_L$. When $D_L \leq D_2 \leq D_U$, the procedure goes to step 249; otherwise, when $D_2 < D_L$ or $D_2 > D_U$, the procedure goes to step 250.

At step S249, the second controller 205 unlocks the heat generator 209. That is, the second power supply 206 is electrically connected to the heat generator 209 and supplies electric power to the heat generator 209 according to the second smoking parameter $D_2$.

One example of unlocking the heat generator 209 may be that the second power supply 206 supplies electric power to the heat generator 209, that is, the second power supply 206 is electrically connected to the heat generator 209 when the user lights the electronic cigarette 2.

At step S250, the second controller 205 locks out the heat generator 209. That is, the second power supply 206 is disconnected from the heat generator 209.

One example of locking out the heat generator 209 may be that the second power supply 206 does not supply power to the heat generator 209 (that is, the heat generator 209 does not generate heat) even when the user lights the electronic cigarette 2.

Compared to the second embodiment, when the user input interface 204 receives the second smoking parameter $D_2$ input by the user, the second controller 205 in the fourth embodiment can further compare the input second smoking parameter $D_2$ with the upper threshold $D_U$ and the lower threshold $D_L$, and lock out or unlock the heat generator 209 accordingly. Thus, damage to the human body and/or the electronic cigarette 2 can be prevented in case the user randomly inputs the second smoking parameter $D_2$ under the manual mode.

In another embodiment, the electronic cigarette 2 can display a first warning signal on the second display device 202 for reminding the user that the input smoking parameter is out of range, during the above step S250. The electronic cigarette 2 can further output the first warning signal to the user through another warning device, such as an indication lamp, a vibrator, or a speaker.

In other embodiments, the submethod of the third embodiment can further be modified according to the fourth embodiment. That is, when the user input interface 204 receives the second smoking parameter $D_2$ input by the user, the second controller 205 can further compare the input second smoking parameter $D_2$ with the upper threshold $D_U$ and the lower threshold $D_L$, and lock out or unlock the heat generator 209 accordingly.

When the aerosol-forming material of the electronic cigarette 2 is tobacco juice, the user needs to add the tobacco juice in the tobacco juice storage container 208 before the heat generator 209 works. The electronic cigarette 2 can further recommend a suitable concentration of nicotine to the user according to the sensed body state of the user. The method for recommending, illustrated by FIG. 7, begins at step 311.

At step S311, the second communication interface 203 receives the sensed body state data of the user from the first communication interface 106. Then, the procedure goes to step S312.

At step S312, the second controller 205 obtains the sensed body state data of the user from the second communication interface 203, and determines a health level L of the user according to the sensed body state data $D_0$ of the user and the relationship between body state data of the user and health levels stored in the second memory 201. Then, the procedure goes to step S313.

At step S313, the second controller 205 determines a first concentration of nicotine $C_0$ according to the determined health level L and the relationship between health levels and first concentrations of nicotine stored in the second memory 201. Then, the procedure goes to step S314.

At step S314, the second display screen 202 displays the determined first concentration of nicotine $C_0$.

The first concentrations of nicotine match the health levels of the user. The first concentrations of nicotine can be set according to at least one of the manufacturer of the electronic cigarette, the health caring platform, the doctor, and the family member.

Thus, the user can add nicotine in the tobacco juice storage container 208, for a concentration that equals to or is less than the determined first concentration. Then, the electronic cigarette 2 can further execute the submethod of any one of the above first to fourth embodiments.

Because the electronic cigarette 2 already receives the sensed body state data $D_0$ of the user and determines the corresponding health level L of the user when recommending the suitable concentration of nicotine to the user, then the same steps can be omitted from the submethod of any one of the above first to fourth embodiments. For example, the method can omit steps S212 and S213 in the first embodiment, the steps S221 and S222 in the second embodiment, the steps S232 and S233 in the third embodiment, and the steps S241 and S242 in the first embodiment.

Figure 7:
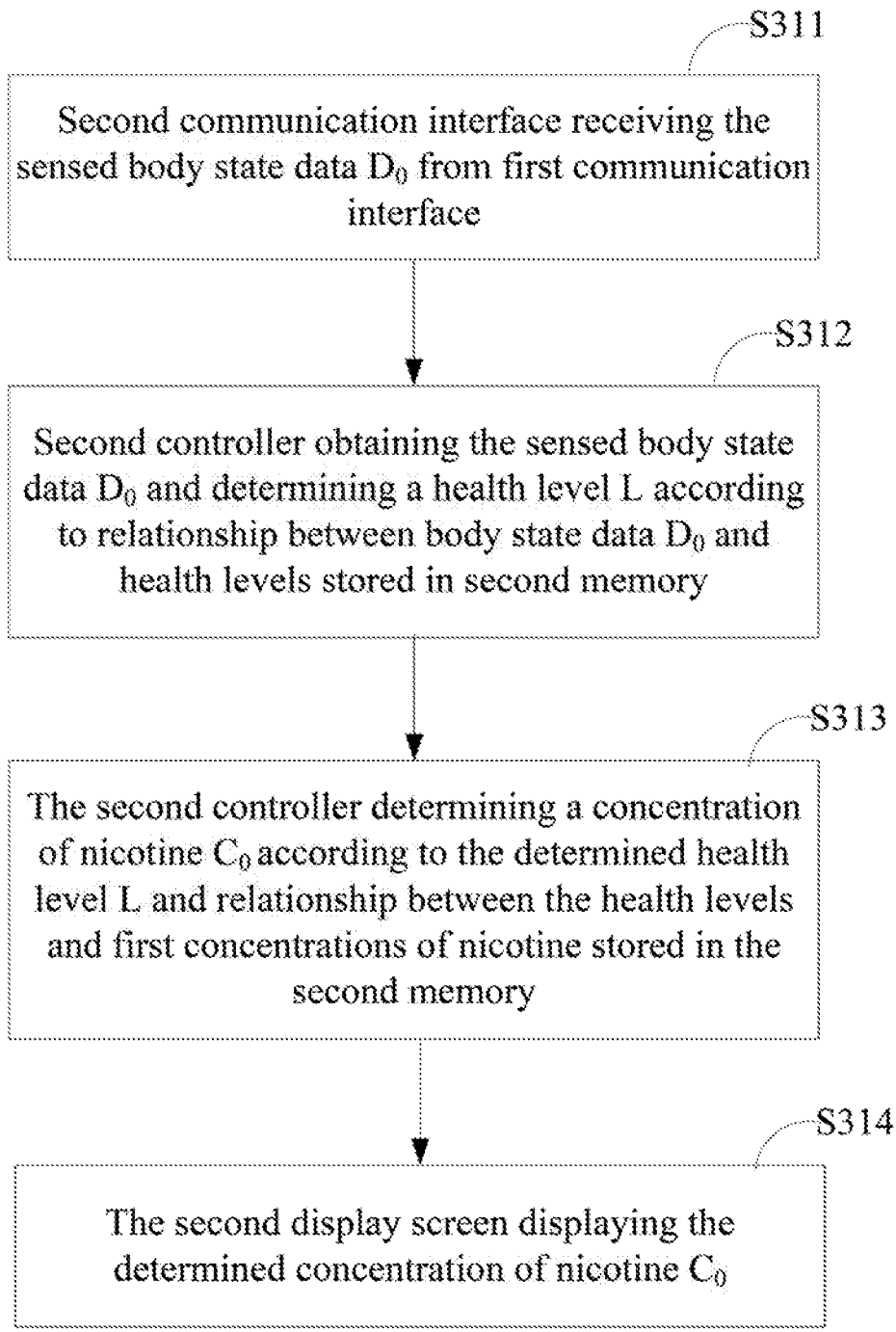
FIG. 7 is a flowchart illustrating a method for recommending suitable concentration of nicotine to the user which is executed before the electronic cigarette control method of FIGS. 3-6.

In other embodiments, nicotine can be replaced by another target element in the submethod of FIG. 7, to cause the second display screen 220 to display the first concentration of the target element $C_0'$.

Figure 8:
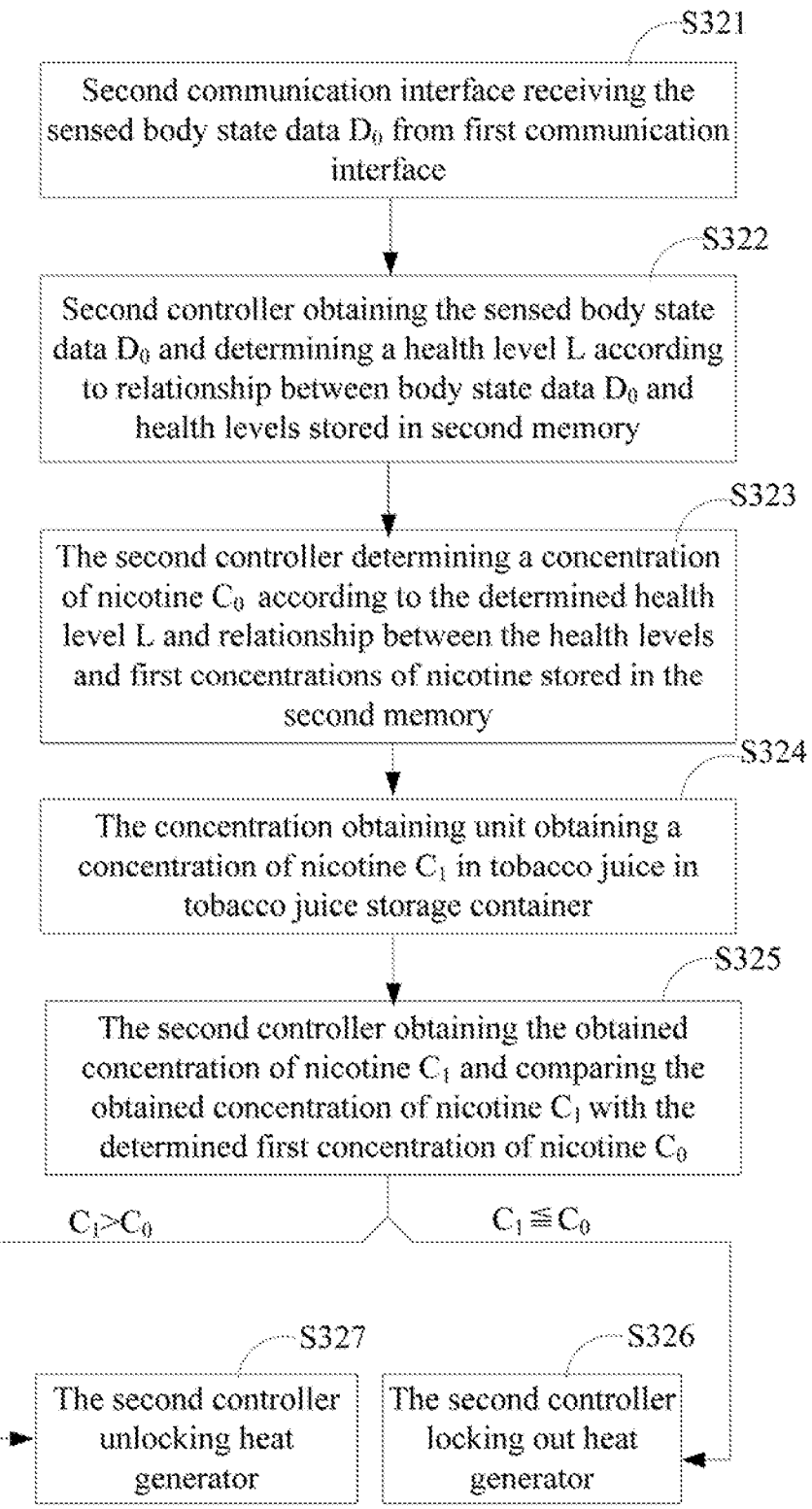
FIG. 8 is a flowchart of a method for controlling the electronic cigarette to operate according to the recommended concentration of nicotine of FIG. 7.

To prevent the user from randomly or mistakenly adding nicotine, to a concentration that does not match the health level of the user, the electronic cigarette 2 can compare the sensed concentration of nicotine $C_1$ with the determined first concentration of nicotine $C_0$, and lock out or unlock the heat generator 209 accordingly. The method, illustrated by FIG. 8, can begin at step S321.

At step S321, the second communication interface 203 receives the sensed body state data $D_0$ of the user from the first communication interface 106. Then, the procedure goes to step S322.

At step S322, the second controller 205 obtains the sensed body state data $D_0$ of the user from the second communication interface 203, and determines a health level L of the user according to the sensed body state data $D_0$ of the user and the relationship between body state data of the user and health levels stored in the second memory 201. Then, the procedure goes to step S323.

At step S323, the second controller 205 determines a first concentration of nicotine $C_0$ according to the determined health level L and the relationship between health levels and first concentrations of nicotine stored in the second memory 201. Then, the procedure goes to step S324.

At step S324, the concentration obtaining unit 207 obtains a concentration of nicotine $C_1$ in the tobacco juice in the tobacco juice storage container 208. Then, the procedure goes to step S325.

At step S325, the second controller 205 obtains the obtained concentration of nicotine $C_1$ from the concentration obtaining unit 207, and compares the obtained concentration of nicotine $C_1$ with the determined first concentration of nicotine $C_0$. If the obtained concentration of nicotine $C_1$ is greater than the determined first concentration of nicotine $C_0$ ($C_1 > C_0$), the procedure goes to step S327, otherwise the procedure goes to step S326 if the obtained concentration of nicotine $C_1$ is less than or equals to the determined first concentration of nicotine $C_0$ ($C_1 \leq C_0$).

At step S326, the second controller 205 locks out the heat generator 209. That is, the second power supply 206 is disconnected from the heat generator 209.

At step S327, the second controller 205 unlocks the heat generator 209. That is, the second power supply 206 is reconnected to the heat generator 209.

In other embodiments, the second controller 205 can further control the second display device 202 to display a second warning signal for reminding the user of a high level of concentration of nicotine during step S326, and that continuing to use the current concentration of nicotine may result in health risk. The electronic cigarette 2 can also output the second warning signal to the user through another warning device, such as an indication lamp, a vibrator, or a speaker.

In other embodiments, the step of obtaining the concentration of nicotine $C_1$ in the tobacco juice in the tobacco juice storage container 208 can be executed before the step of determining the first concentration of nicotine $C_0$. That is, the step S324 can be executed before step S321 to step S323. Finally, step S325 to step S327 are executed.

When the second controller 205 locks out the heat generator 209, the electronic cigarette 2 stops executing the submethod in any one of the first to fourth embodiments. When the second controller 205 unlocks the heat generator 209, the electronic cigarette 2 can continue to execute the submethod in any one of the first to fourth embodiments, to control the heat generator 209 to operate.

Because the electronic cigarette 2 already receives the sensed body state data $D_0$ of the user and determines the corresponding health level L of the user during determining the first concentration of nicotine $C_0$, the same steps can be omitted when electronic cigarette 2 further executes the submethod of any one of the above first to fourth embodiments. For example, the method can omit steps S212 and S213 in the first embodiment, the steps S221 and S222 in the second embodiment, the steps S232 and S233 in the third embodiment, and the steps S241 and S242 in the first embodiment.

Before the user adds the tobacco juice, the electronic cigarette 2 can first execute the submethod of FIG. 7 to cause the second display screen 202 of the electronic cigarette 2 to display to the user the determined first concentration of nicotine $C_0$. After the user adds the tobacco juice, because the electronic cigarette 2 already receives the sensed body state data $D_0$ of the user and determines the corresponding health level L of the user and the first concentration of nicotine $C_0$, the step S324 is executed to obtain the concentration of nicotine $C_1$ in the tobacco juice, but steps S321 to S323 can be omitted.

In another embodiment, the first communication interface 103 and the second communication interface 203 are connected to each other through a third-party device (not shown). The step of the first communication interface 106 and the second communication interface 203 establishing data connection to transmit the sensed body state data $D_0$ of the user can be changed to the step of the first controller 102 controlling the first communication interface 106 and the third-party device to establish data connection with each other. The first communication interface 106 can be controlled to transmit the sensed body state data $D_0$ of the user to the third-party device. Furthermore, the second communication interface 203, when controlled by the second controller 205, can establish data connection with the third-party device, receive the sensed body state data $D_0$ of the user from the third-party device, and transmit the sensed body state data $D_0$ of the user to the second controller 205.

In yet another embodiment, the relationship between the body state data of the user and the health levels can also be stored in the first memory 105 of the wearable electronic device 1 or in the third-party device. The first controller 102 or the third-party device can determine a health level L of the user according to the sensed body state data $D_0$ of the user and the relationship between the body state data of the user and health levels, and transmit the determined health level L of the user to the electronic cigarette 2. Thus, the step of determining the health level L of the user is added into the submethod executed by the first controller 102 or the third-party device. The step of transmitting the sensed body state data $D_0$ of the user is replaced by the step of transmitting the determined health level L of the user. Accordingly, the step of the second communication interface 203 receiving the sensed body state data $D_0$ of the user is replaced by the step of receiving the determined health level L of the user. The step of the second controller 205 determining the health level L of the user is omitted.

In yet another embodiment, the relationship between the body state data of the user and health levels, and the relationship between the health levels and first smoking parameters can both be stored in the first memory 105 of the wearable electronic device 1 or in the third-party device. The first controller 102 or the third-party device can determine a health level L of the user according to the sensed body state data $D_0$ of the user and the relationship between the body state data of the user and health levels, determine a first smoking parameter $D_1$ according to the determined health level L of the user and the relationship between the health levels and first smoking parameters, and transmit the determined first smoking parameter $D_1$ to the electronic cigarette 2. Thus, the step of determining the health level L of the user and the first smoking parameter $D_1$ is added into the submethod executed by the first controller 102 or the third-party device. The step of transmitting the sensed body state data $D_0$ of the user is replaced by the step of transmitting the determined first smoking parameter $D_1$. Accordingly, the step of the second communication interface 203 receiving the sensed body state data $D_0$ of the user is replaced by the step of receiving the determined first smoking parameter $D_1$. The step of the second controller 205 determining the health level L of the user and the first smoking parameter $D_1$ is omitted.

In other embodiments, the first concentration of the target element $C_0'$ can also be determined and transmitted by the wearable electronic device 1 or the third-party device.

In an embodiment, the second memory 201 of the electronic cigarette 2 further stores at least one pattern image, at least one growth-value range, at least one grade, and a growth value. An original growth value equals to zero. These values relate to an electronic pet. The second memory 201 further stores a relationship between growth-value range(s) and grade(s) of the electronic pet, and a relationship between the grade(s) and pattern image(s) of the electronic pet. The second controller 205 further determines whether the recommended smoking scheme is executed by the user. If the recommended smoking scheme is executed by the user, the growth value of the electronic pet is increased by 1. If the recommended smoking scheme is not executed by the user, the growth value of the electronic pet is not increased. The second controller 205 further determines the growth-value range in which the growth value falls in, determines the grade of the electronic pet according to the relationship between the growth-value range(s) and the grade(s) of the electronic pet, and determines a pattern image of the electronic pet according to the relationship between the grade(s) and the pattern images of the electronic pet. The second display screen 202 then displays the determined pattern image.

The second memory 201 can further store at least one electronic pet. The user can select one electronic pet to be kept through the user input interface 204.

For example, the electronic pet can be a cat, a dog, or a rabbit. The user can select the electronic pet cat through the user input interface 204. The pattern images of the electronic pet cat can include a pattern image of young cat and a pattern image of grown-up cat. The growth-value ranges can include a growth-value range of [0, 1000] and a growth-value range of [1001, +∞). The grades can include a first grade and a second grade. The growth-value range of [0, 1000] corresponds to the first grade, and the growth-value range of [1001, +∞] corresponds the second grade. The first grade corresponds to the pattern image of young cat, and the second grade corresponds to the pattern image of a grown-up cat. When the electronic pet cat grows with a growth value of 1020, the second controller 205 determines that the growth value of 1020 falls in the range of [1001, +∞]. Then, the second controller 205 determines the grade of the electronic pet grade to be the second grade, and the pattern image of the electronic pet to be the pattern image of grown-up cat. The second controller 205 then controls the second display screen 202 to display the pattern image of grown-up cat.

Figure 9:
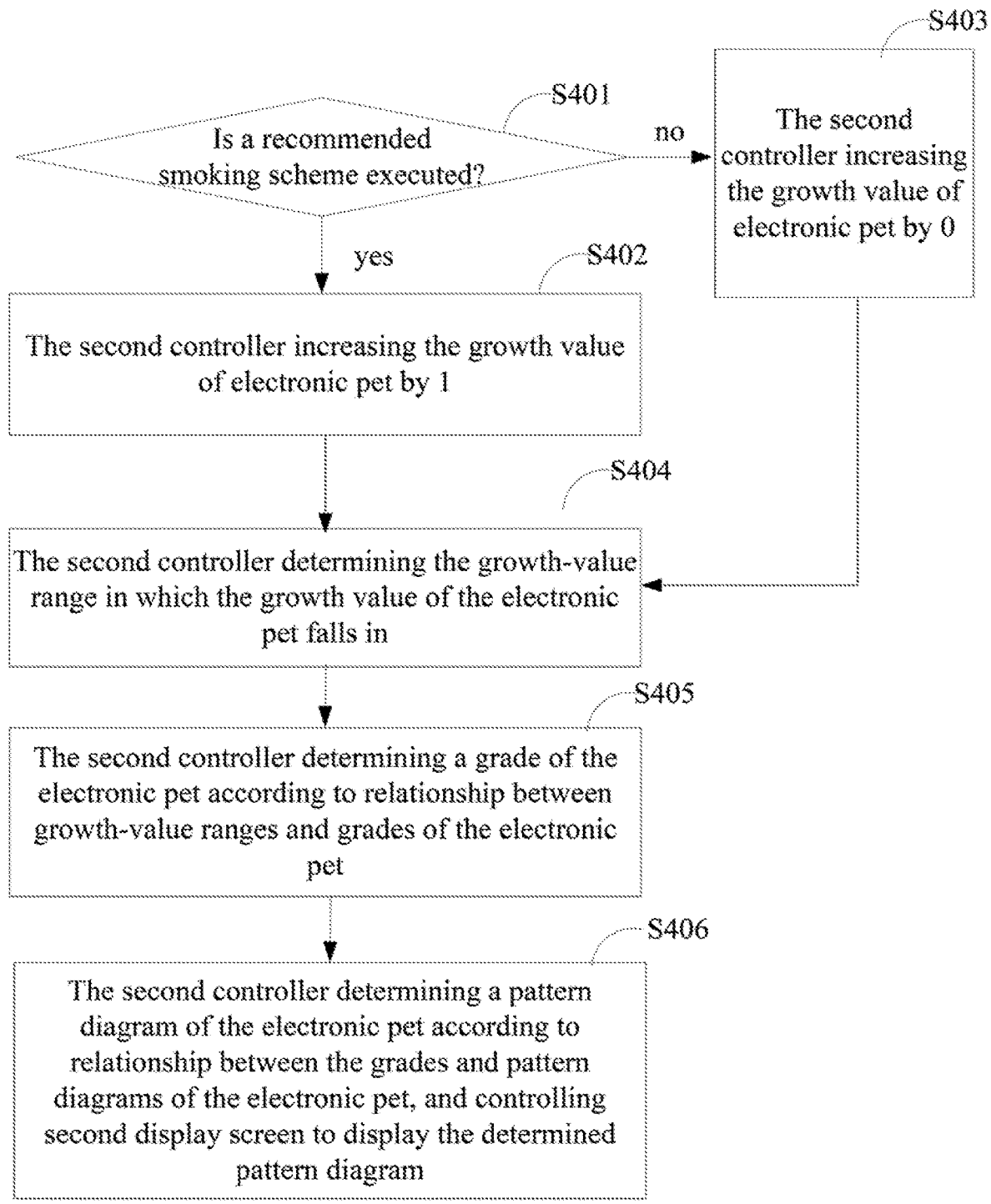
FIG. 9 is a flowchart illustrating an upgrading method for an electronic pet.

In an embodiment, the original growth value of the electronic pet equals to zero. Referring to FIG. 9, an upgrading method for the electronic pet begins at step S401.

At step S401, the second controller 205 determines whether the recommended smoking scheme is executed by the user. If yes, the procedure goes to step S402, otherwise, the procedure goes to step S403.

At step S402, the second controller 205 increases the growth value of the electronic pet by 1. Then, the procedure goes to step S404.

At step S403, the second controller 205 increases the growth value of the electronic pet by 0. Then, the procedure goes to step S404.

At step S404, the second controller 205 determines the growth-value range in which the growth value falls in. Then, the procedure goes to step S405.

At step S405, the second controller 205 determines the grade of the electronic pet according to the relationship between the growth-value range(s) and the grade(s) of the electronic pet. Then, the procedure goes to step S406.

At step S406, the second controller 205 determines a pattern image of the electronic pet according to the relationship between grade(s) and pattern images of the electronic pet, and controls the second display screen 202 to display the determined pattern image.

The second controller 205 can determine whether the recommended smoking scheme is executed by the user after each smoking session.

In an embodiment, executing the recommended smoking scheme is that the electronic cigarette 2 works according to the determined first smoking parameter $D_1$.

In another embodiment, when the aerosol-forming material of the electronic cigarette 2 is tobacco juice, executing the recommended smoking scheme indicates that the target element of the electronic cigarette 2 meets preset requirements. For example, when the target element is nicotine, the concentration of nicotine $C_1$ in the tobacco juice is less than or equals to the determined first concentration of nicotine $C_0$, and the electronic cigarette 2 operates according to the determined first smoking parameter $D_1$.

In other embodiments, the wearable electronic device 1 can synchronously display the determined pattern image of the electronic pet. In detail, the second communication interface 203 transmits the determined pattern image of the electronic pet to the first communication interface 106. The first controller 102 obtains the determined pattern image of the electronic pet from the first communication interface 106, and controls the first display device 104 to synchronously display the determined pattern image of the electronic pet.

Figure 10:
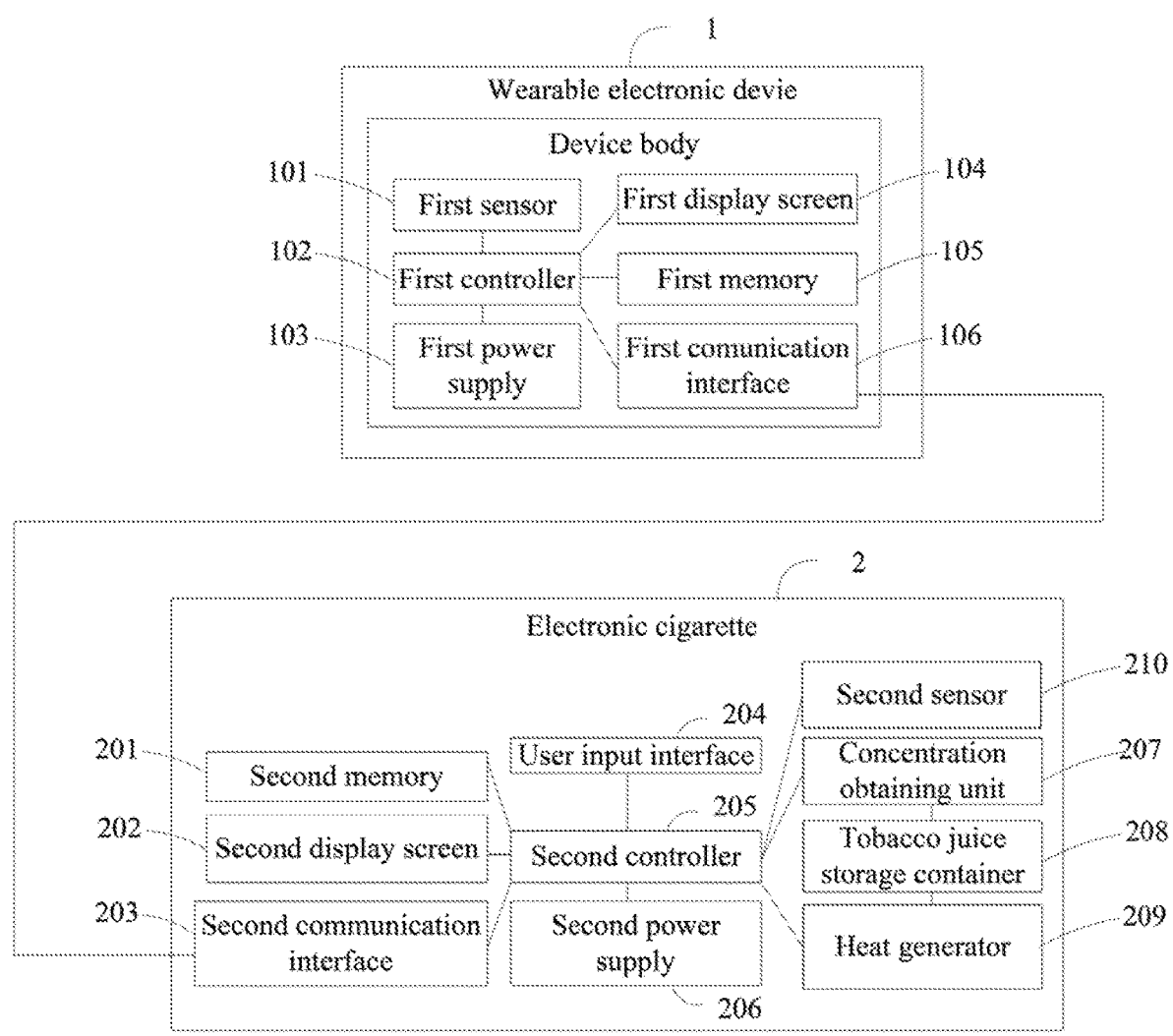
FIG. 10 is a block diagram illustrating a second embodiment of an electronic cigarette control system including an electronic cigarette and a wearable electronic device.

The grown up version of the electronic pet may urge the user to execute the recommended smoking scheme, and may increase the user experience by allowing the user to choose the smoking scheme suitable for the body state data of the user FIG. 10 illustrates a second embodiment of an electronic cigarette control system 200. Difference compared to the electronic cigarette control system 100 of the first embodiment is that the electronic cigarette 2 of the electronic cigarette control system 200 further includes a second sensor 210 that is electrically connected to the second controller 205. The second sensor 210 can sense the body state of the user to obtain data thereof.

The second sensor 210 can include at least one of an accelerometer, an optical heart rate monitor, a skin electric reaction sensor, a bioelectrical impedance sensor, and a pulse wave sensor. The body state data of the user includes at least one of a number of steps taken by the user, a heart rate, a perspiration rate, and a pulse of the user. The accelerometer can record the number of steps of the user. The optical heart rate monitor can monitor the heart rate of the user. The skin electric reaction sensor can sense the perspiration rate of the user. The bioelectrical impedance sensor can monitor the blood flow based on the inherent impedance of the biological body, and transfer the sensed blood flowrate to the heart rate, the respiration rate, and the skin electrical reaction index. The pulse wave sensor can sense the pulse of the user.

Because both the wearable electronic device 1 and the electronic cigarette 2 can sense the body state data $D_0$ of the user, the user can select one or both of the wearable electronic device 1 and the electronic cigarette 2 to sense the body state data $D_0$ of a single person or different persons. Accordingly, the electronic cigarette 2 includes a single-person mode and a multi-person interaction mode.

If a user selects the single-user mode, it indicates that the electronic cigarette 2 and the wearable electronic device 1 are used by a single person. That is, the sensed body state data $D_0$ of the user of the electronic cigarette 2 and the sensed body state data $D_0$ of the user of the wearable electronic device 1 are from a single person. In detail, when the wearable electronic device 1 transmits the sensed body state data $D_0$ of the user to the electronic cigarette 2, the second display screen 202 displays the sensed body state data $D_0$ of the user from the electronic cigarette 2 and the sensed body state data $D_0$ of the user from the wearable electronic device 1. Then, the user can select whether to integrate the sensed body state data $D_0$ of the user from the electronic cigarette 2 and the sensed body state data $D_0$ of the user from the wearable electronic device 1. When integrated, the second controller 205 determines the first smoking parameter $D_1$ according to the integrated body state data (labeled as: $D_0'$) of the user. Otherwise, the user can select one of the sensed body state data $D_0$ of the user according to actual need. The second controller 205 then determines the first smoking parameter $D_1$ according to the selected body state data $D_0$ of the user.

When the aerosol-forming material of the electronic cigarette 2 is tobacco juice, the second controller 205 can determine the first concentration of the target element $C_0'$ according to the integrated body state data $D_0'$ or the selected body state data $D_0$ of the user.

Thus, by selecting whether to integrate the body state data $D_0$ of the user, the electronic cigarette control system 100 can be more personalized.

Integration of the body state data of the user can include, but is not limited to, the example integrations, such as a first integration and a second integration.

The first integration may be that the electronic cigarette 2 calculates an average of a same type of the sensed body state data $D_0$ of the user. For example, when the number of steps taken by the user sensed by the electronic cigarette 2 equals to 7000, and the number of steps taken by the user sensed by the wearable electronic device 1 equals to 8000, the integrated number of steps taken by the user equals to 7500. Different factors of the sensed body state data $D_0$ of the user are not integrated. For example, the heart rate sensed by the electronic cigarette 2 is not integrated with the number of steps taken by the user sensed by the wearable electronic device 1.

The second integration may be that the electronic cigarette 2 chooses a maximum value from a same type of the sensed body state data $D_0$ of the user. For example, the number of steps taken by the user sensed by the electronic cigarette 2 equals to 7000, and the number of steps taken by the user sensed by the wearable electronic device 1 equals to 8000. Thus, the integrated number of steps taken by the user equals to 8000. Different factors of the sensed body state data $D_0$ of the user are also not integrated.

In other embodiments, the wearable electronic device 1 can also synchronously displays the integrated body state data $D_0'$ or the unintegrated body state data $D_0$ of the user. The second communication interface 203 can transmit the integrated body state data $D_0'$ of the user and/or the sensed body state data $D_0$ of the user from the electronic cigarette 2 to the first communication interface 106. The first controller 102 obtains the integrated body state data $D_0'$ and/or the sensed body state data $D_0$ of the user from the first communication interface 106, and synchronously displays the integrated body state data $D_0'$ and/or the sensed body state data $D_0$ of the user from the electronic cigarette 2.

In other embodiments, the user can select whether to integrate the sensed body state data $D_0$ of the user through the wearable electronic device 1. The wearable electronic device 1 also includes a user input interface. The electronic cigarette 2 transmits the sensed body state data $D_0$ of the user to the wearable electronic device 1. The user can select whether to integrate the sensed body state data $D_0$ of the user through the user input interface of the wearable electronic device 1. The first controller 102 may or may not integrate the sensed body state data $D_0$ of the user accordingly to the selection.

When the user selects the multi-person interaction mode, it indicates that the electronic cigarette 2 and the wearable electronic device 1 are used by different persons. Thus, the sensed body state data $D_0$ of the user of different persons can be compared. In detail, when the wearable electronic device 1 transmits the sensed body state data $D_0$ of the user to the electronic cigarette 2, the second display screen 202 compares the sensed body state data $D_0$ of the user from the electronic cigarette 2 with the sensed body state data $D_0$ of the user from the wearable electronic device 1, and displays a comparison result accordingly. Thus, the user experience during interaction can further be improved.

In other embodiments, the wearable electronic device 1 can also synchronously display the comparison result. The second communication interface 203 can transmit the comparison result to the first communication interface 106. The first controller 102 obtains the comparison result from the first communication interface 106, and synchronously displays the comparison result.

In other embodiments, the electronic cigarette 2 can further transmit the sensed body state data $D_0$ of the user to the wearable electronic device 1. The first controller 102 compares the sensed body state data $D_0$ of the user from the electronic cigarette 2 with the sensed body state data $D_0$ of the user from the wearable electronic device 1, and displays the comparison result.

In a third embodiment of an electronic cigarette control system 100, the wearable electronic device 1 and the electronic cigarette 2 can establish a wireless connection, such as connection by at least one of cellular network, WI-FI, infrared, BLUETOOTH, ZIGBEE, and NFC. Then, the electronic cigarette 2 can transmit an anti-loss signal to the wearable electronic device 1. The wearable electronic device 1 can determine whether the electronic cigarette 2 has risk of loss by determining an intensity (labeled as: $I_1$) of the anti-loss signal.

The user input interface 204 is for the user to input a signal for initiating an anti-loss mode of the electronic cigarette 2 (hereinafter, "anti-loss mode initiating signal"), and transmits the anti-loss mode initiating signal to the second controller 205.

The second controller 205 controls the second communication interface 203 and the first communication interface 106 to establish data connection with each other in response to the anti-loss mode initiating signal, and controls the second communication interface 203 to periodically transmit an anti-loss signal to the first communication interface 106. For example, the anti-loss signal can be transmitted at three minute intervals.

The first controller 102 controls the first communication interface 106 to establish data connection with the second communication interface 203 and to receive the anti-loss mode initiating signal from the second communication interface 203.

The first memory 105 stores a preset intensity (labeled as: $I_0$).

The first controller 102 obtains the anti-loss mode initiating signal from the second communication interface 203, and compares an intensity $I_1$ of the anti-loss signal with the preset intensity $I_0$ stored in the first memory 105. When the intensity $I_1$ of the anti-loss signal is greater than or equals to the preset intensity $I_0$, the first controller 102 determines that the electronic cigarette 2 is not lost. When the intensity $I_1$ of the anti-loss signal is less than the preset intensity $I_0$, the first controller 102 determines that the electronic cigarette 2 may be lost, and controls the first display screen 104 to display a third warning signal for reminding the user that the electronic cigarette 2 may be lost.

In other embodiments, the wearable electronic device 1 can output the third warning signal to the user through another warning device, such as an indication lamp, a vibrator, or a speaker.

Figure 11:
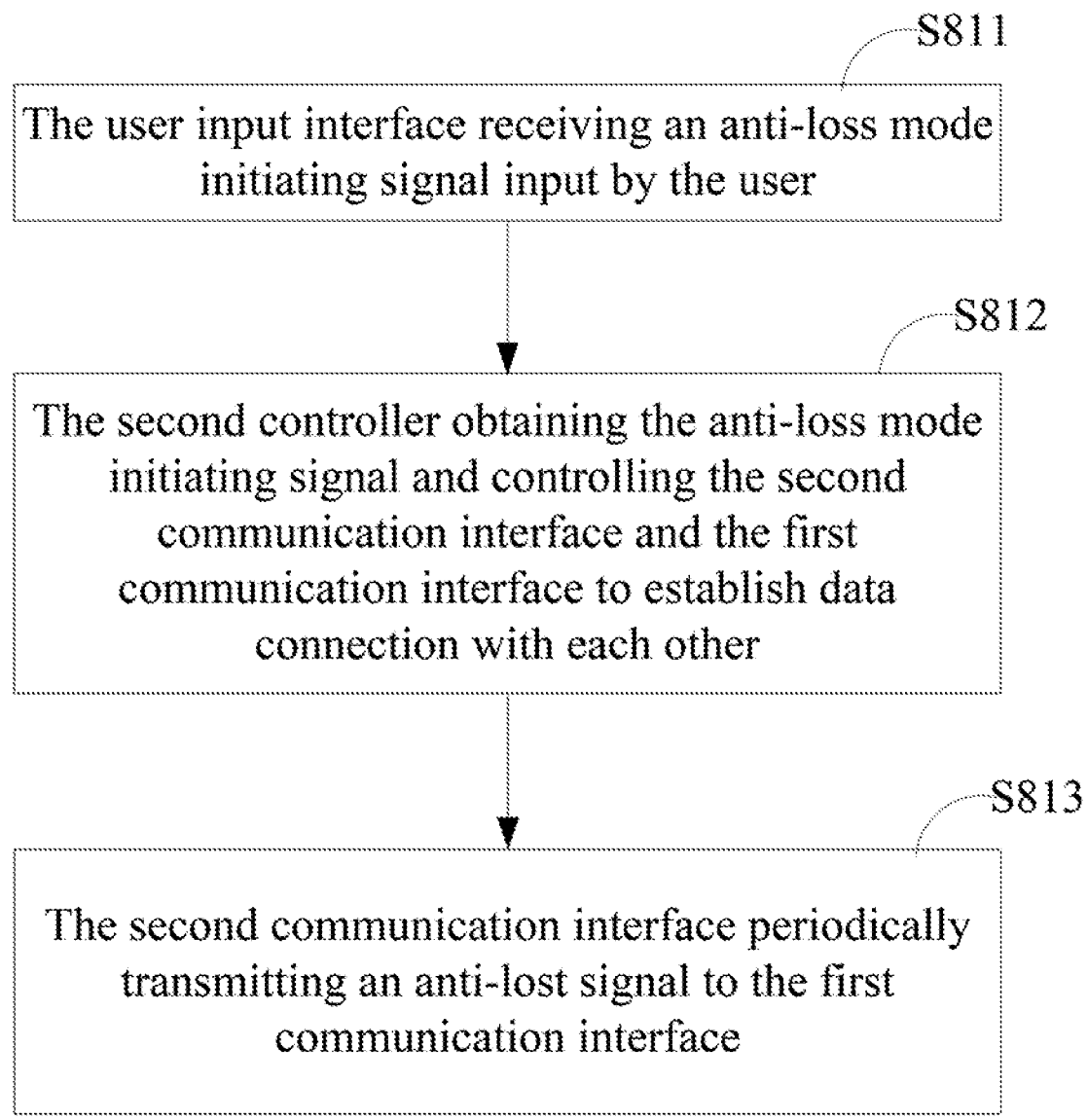
FIG. 11 is a flowchart illustrating an electronic cigarette anti-loss method executed by the electronic cigarette of FIG. 10.

FIG. 11 illustrates an anti-loss method for electronic cigarette executed by the electronic cigarette control system 200. The anti-loss method includes a submethod executed by the electronic cigarette 2 and a submethod executed by the wearable electronic device 1. The submethod executed by the electronic cigarette 2 can begin at step S811.

At step S811, the user input interface 204 receives an anti-loss mode initiating signal input by the user for initiating an anti-loss mode of the electronic cigarette 2. Then, the procedure goes to S812.

At step S812, the second controller 205 obtains the anti-loss mode initiating signal from the user input interface 204, and controls the second communication interface 203 and the first communication interface 106 to establish data connection with each other in response to the anti-loss mode initiating signal. Then, the procedure goes to S813.

At step S813, the second communication interface 203 periodically transmits an anti-loss signal to the first communication interface 106.

Figure 12:
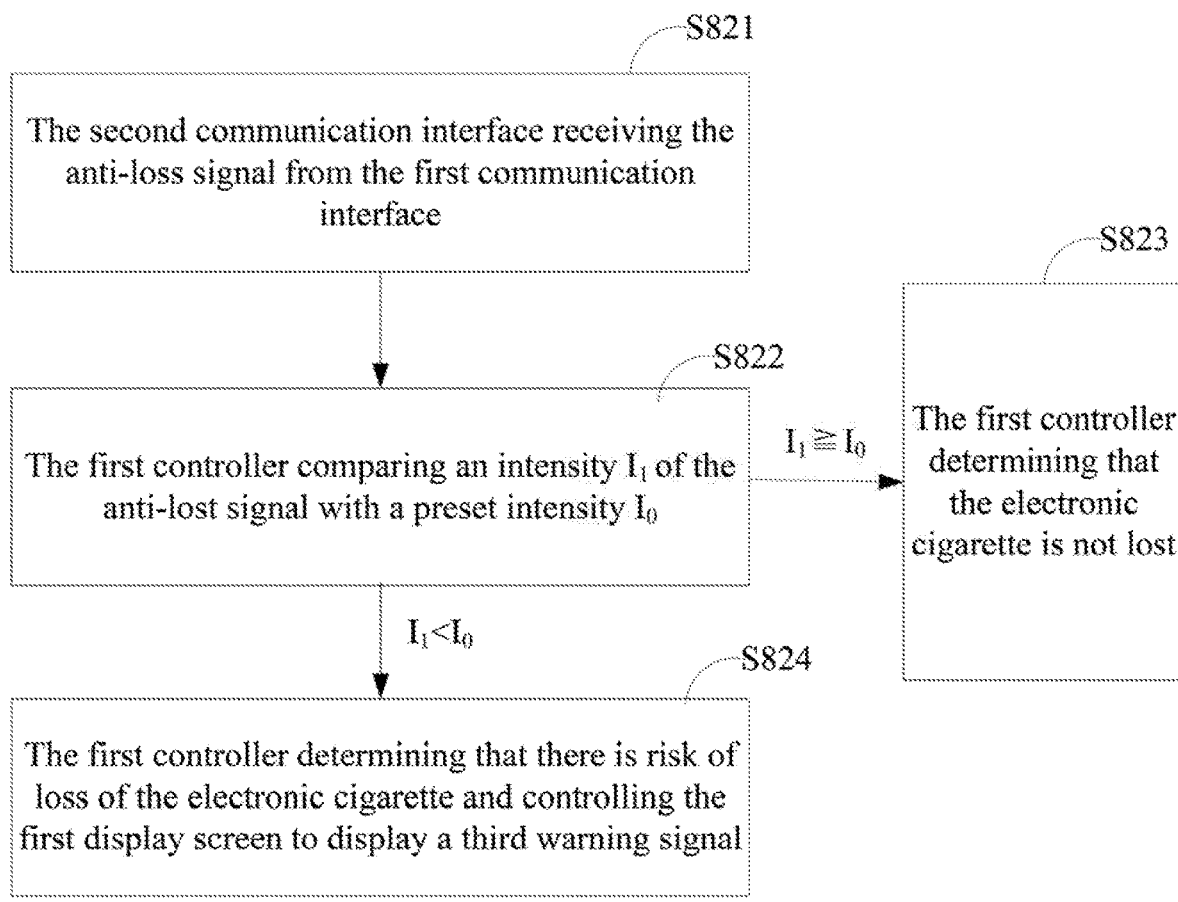
FIG. 12 is a flowchart illustrating an electronic cigarette anti-loss method executed by the wearable electronic device of FIG. 10.

FIG. 12 illustrates a submethod of the anti-loss method executed by the wearable electronic device 1. The submethod can begin at step S821.

At step S821, the first communication interface 106 receives the anti-loss signal from the second communication interface 203. Then, the procedure goes to S822.

At step S822, the first controller 102 obtains the anti-loss signal from the first communication interface 106, and compares an intensity $I_1$ of the anti-loss signal with the preset intensity $I_0$ stored in the first memory 105. If the intensity $I_1$ of the anti-loss signal is greater than or equals to the preset intensity $I_0$ ($I_1 \geq I_0$), the procedure goes to S823. If the intensity $I_1$ of the anti-loss signal is less than the preset intensity $I_0$ ($I_1 < I_0$), the procedure goes to S824.

At step S823, the first controller 102 determines that the electronic cigarette 2 is not lost.

At step S824, the first controller 102 determines that the electronic cigarette 2 has risk of loss, and controls the first display screen 104 to display a third warning signal.

The wearable electronic device 1 can display a third warning signal for reminding the user that the electronic cigarette 2 has risk of loss, when the intensity $I_1$ of the anti-loss signal is less than the preset intensity $I_0$. Thus, the risk of loss of the electronic cigarette 2 can be reduced.

Figure 13:
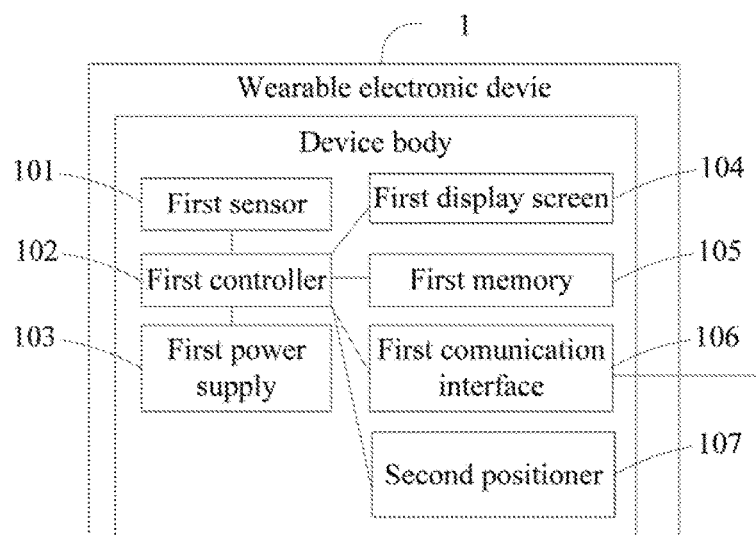
FIG. 13 is a block diagram illustrating a third embodiment of an electronic cigarette control system including an electronic cigarette and a wearable electronic device.
Figure 13:
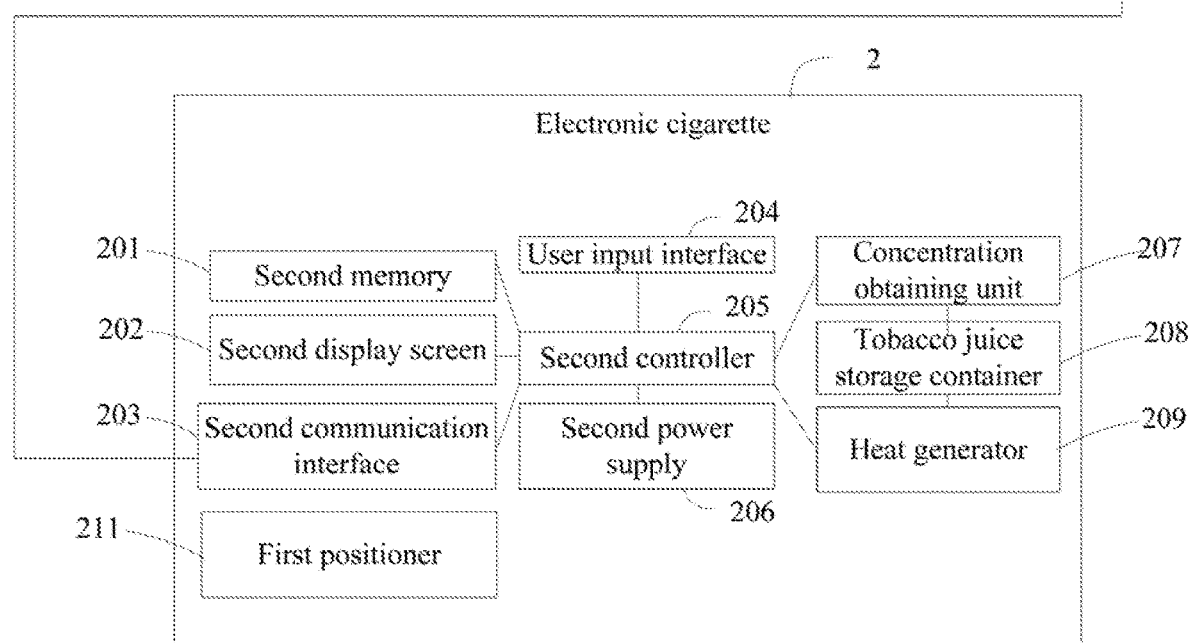

FIG. 13 illustrates a third embodiment of an electronic cigarette control system 300 having an anti-loss function. Difference compared to the electronic cigarette control system 200 of the second embodiment is that the wearable electronic device 1 of the electronic cigarette control system 300 determines whether the electronic cigarette 2 has risk of loss by comparing a distance (labeled as: $L_1$) between the wearable electronic device 1 and the electronic cigarette 2. If the distance $L_1$ is established, such distance $L_1$ is compared with a preset safe distance (labeled as: $L_0$). In detail, the electronic cigarette 2 further includes a first positioner 211. The first positioner 211 can periodically obtain a first position of the electronic cigarette 2. For example, the first positioner 211 can obtain the first position of the electronic cigarette 2 every three minutes. The wearable electronic device 1 further includes a second positioner 107.

The user input interface 204 is for the user to input an anti-loss mode initiating signal.

The second controller 205 obtains the an anti-loss mode initiating signal from the user input interface 205, and controls the second communication interface 203 and the first communication interface 106 to establish data connection with each other in response to the anti-loss mode initiating signal, and controls the first positioner 211 to periodically obtain the first position of the electronic cigarette 2. The second controller 205 further controls the second communication interface 203 to transmit the obtained first position of the electronic cigarette 2 to the first communication interface 106. In detail, each time the first positioner 211 obtains the first position of the electronic cigarette 2, the second controller 205 controls the second communication interface 203 to transmit the obtained first position of the electronic cigarette 2.

The first communication interface 106, controlled by the first controller 102, establishes data connection with the second communication interface 203, and receives the obtained first position from the second communication interface 203.

The first memory 105 stores a preset safe distance $L_0$.

The first controller 102 controls the first communication interface 106 and the second communication interface 203 to establish data connection with each other in response to the obtained first position. The first controller 102 further controls the second positioner 107 to obtain a second position of the wearable electronic device 1, calculates distance $L_1$ between the obtained first position of the electronic cigarette 2 and the obtained second position of the wearable electronic device 1, and compares the calculated distance $L_1$ with the preset safe distance $L_0$. When the calculated distance $L_1$ is less than or equals to the preset safe distance $L_0$, the first controller 102 determines that the electronic cigarette 2 is not lost. When the calculated distance $L_1$ is greater than the preset safe distance $L_0$, the first controller 102 determines that the electronic cigarette 2 has risk of loss, and controls the first display screen 104 to display a third warning signal for reminding the user that the electronic cigarette 2 may be lost.

The first positioner 211 can be a GPS positioner that can detect the GPS coordinate of the electronic cigarette 2. The second positioner 107 can be a GPS positioner that can detect the GPS coordinate of the wearable electronic device 1.

The wearable electronic device 1 and the electronic cigarette 2 can establish a wireless connection.

In other embodiments, the wearable electronic device 1 can output the third warning signal to the user through another warning device, such as an indication lamp, a vibrator, or a speaker.

Figure 14:
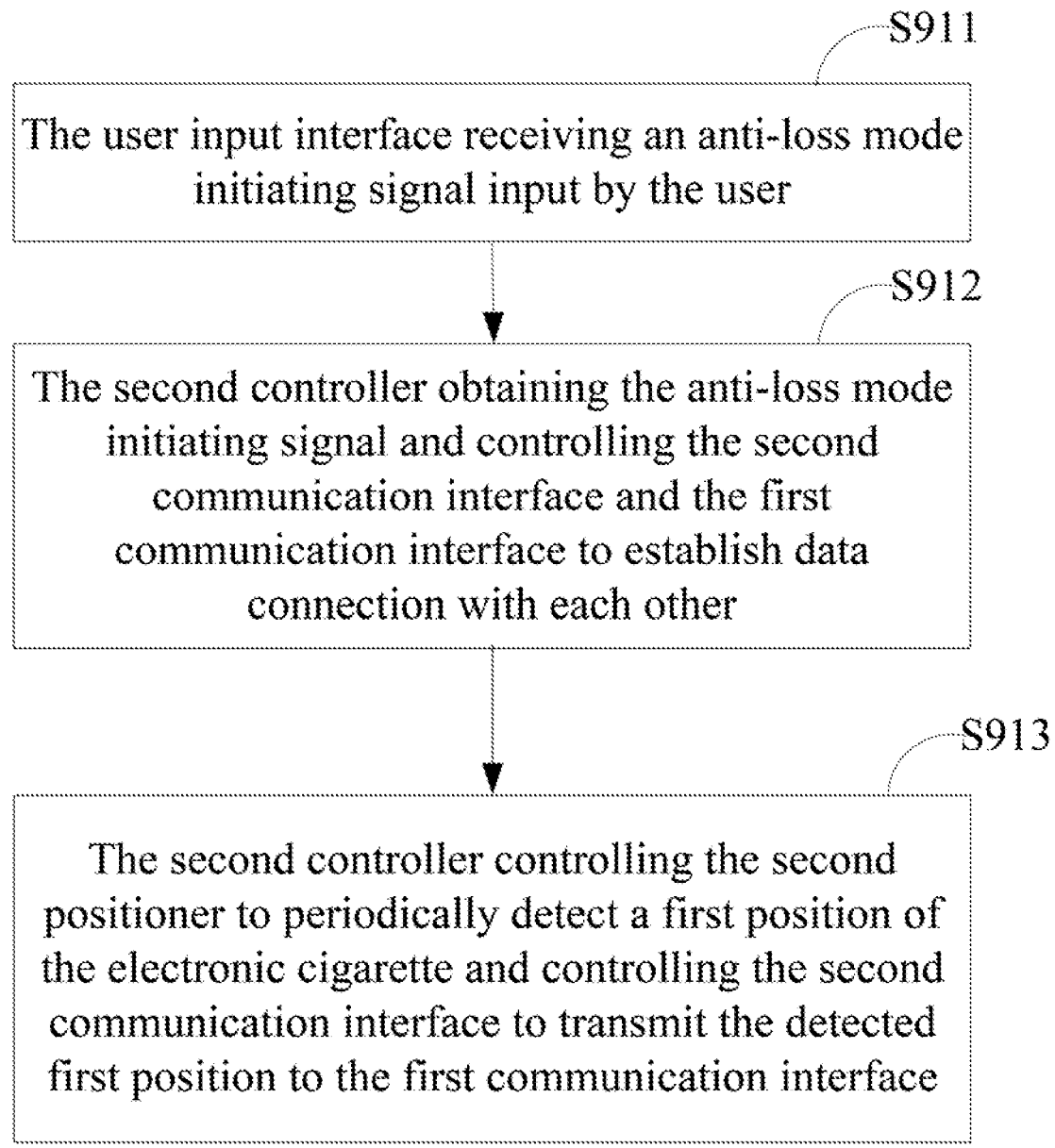
FIG. 14 is a flowchart illustrating an electronic cigarette anti-loss method executed by the electronic cigarette of FIG. 13.

FIG. 14 illustrates an anti-loss method executed by the electronic cigarette control system 300. The anti-loss method includes a submethod executed by the electronic cigarette 2 and a submethod executed by the wearable electronic device 1. The submethod executed by the electronic cigarette 2 can begin at step S811.

At step S911, the user input interface 204 receives an anti-loss mode initiating signal input by the user. Then, the procedure goes to step S912.

At step S912, the second controller 205 obtains the anti-loss mode initiating signal from the user input interface 204, and controls the second communication interface 203 and the first communication interface 106 to establish data connection with each other. Then, the procedure goes to step S913.

At step S913, the second controller 205 controls the first positioner 211 to periodically obtain the first position of the electronic cigarette 2, and controls the second communication interface 203 to transmit the obtained first position of the electronic cigarette 2 to the first communication interface 106.

Figure 15:
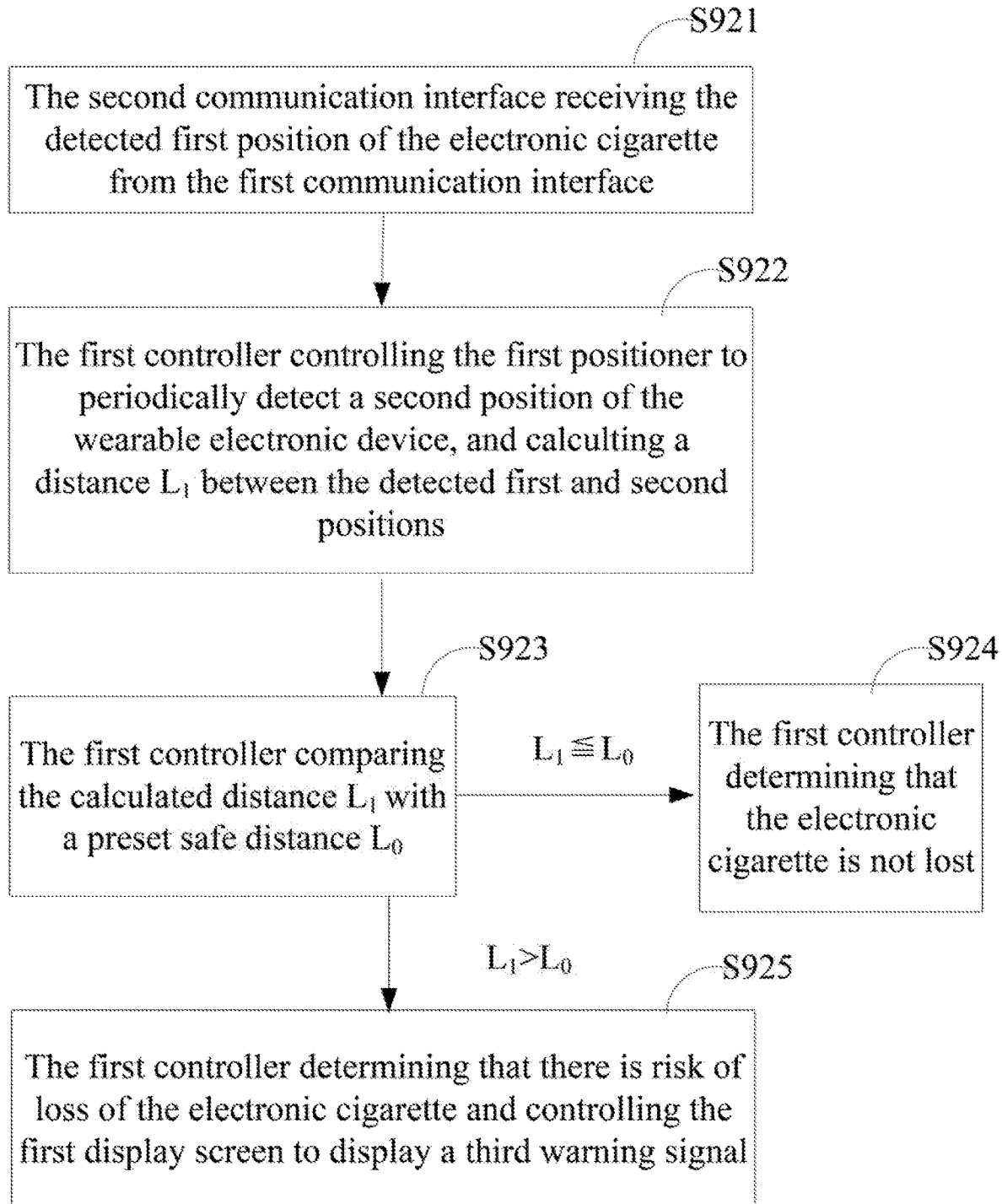
FIG. 15 is a flowchart illustrating an electronic cigarette anti-loss method executed by the wearable electronic device of FIG. 13.

FIG. 15 illustrates a submethod of the anti-loss method executed by the wearable electronic device 1. The submethod can begin at step S921.

At step S921, the first communication interface 106 receives the obtained first position of the electronic cigarette 2 from the second communication interface 203. Then, the procedure goes to step S922.

At step S922, the first controller 102 obtains the obtained first position of the electronic cigarette 2 from the first communication interface 106, controls the second positioner 107 to obtain a second position of the wearable electronic device 1, and calculates a distance $L_1$ between the obtained first position of the electronic cigarette 2 and the obtained second position of the wearable electronic device 1. Then, the procedure goes to step S923.

At step S923, the first controller 102 compares the calculated distance $L_1$ with the preset safe distance $L_0$. When the calculated distance $L_1$ is less than or equals to the preset safe distance $L_0$ ($L_1 \leq L_0$), the procedure goes to step S924. When the calculated distance $L_1$ is greater than the preset safe distance $L_0$ ($L_1 > L_0$), the procedure goes to step S925.

At step S924, the first controller 102 determines that the electronic cigarette 2 is not lost.

At step S925, the first controller 102 determines that the electronic cigarette 2 has risk of loss, and controls the first display screen 104 to display a third warning signal.

The wearable electronic device 1 can display a third warning signal for reminding the user that the electronic cigarette 2 has risk of loss, when the calculated distance $L_1$ is greater than the preset safe distance $L_0$. Thus, the risk of loss of the electronic cigarette 2 can be reduced.

Figure 16:
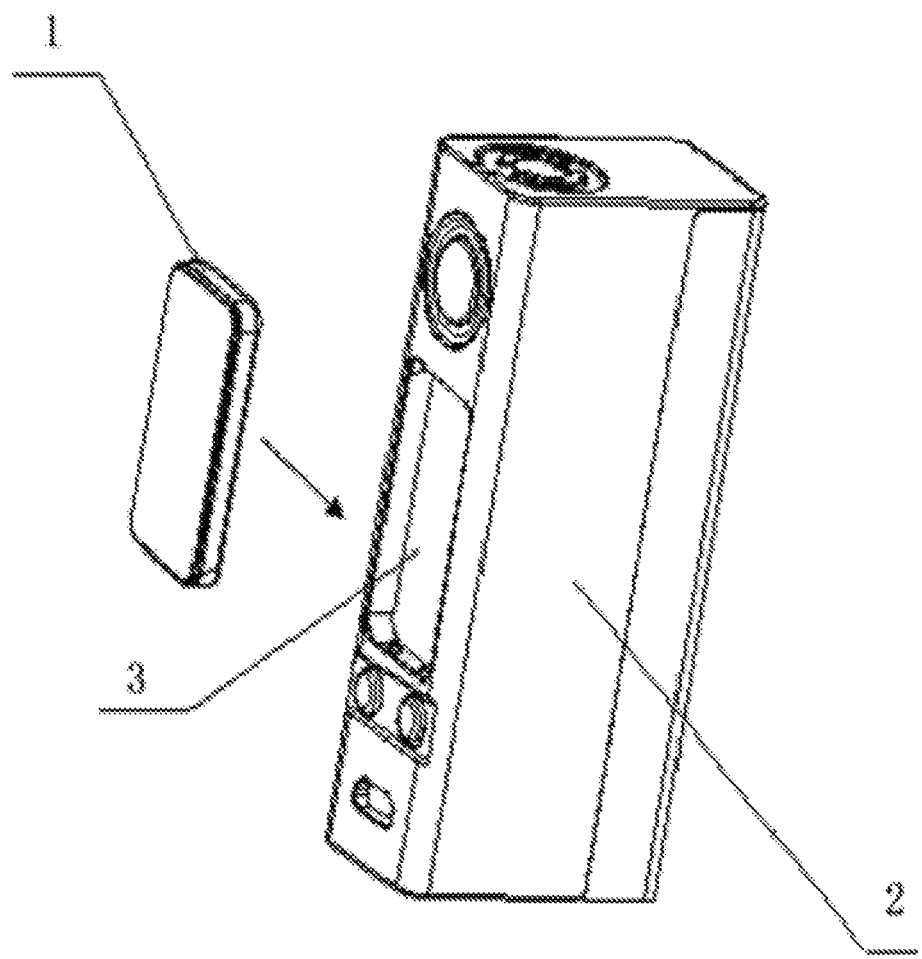
FIG. 16 is a diagram illustrating a fourth embodiment of an electronic cigarette control system including an electronic cigarette and a wearable electronic device.
Figure 17:
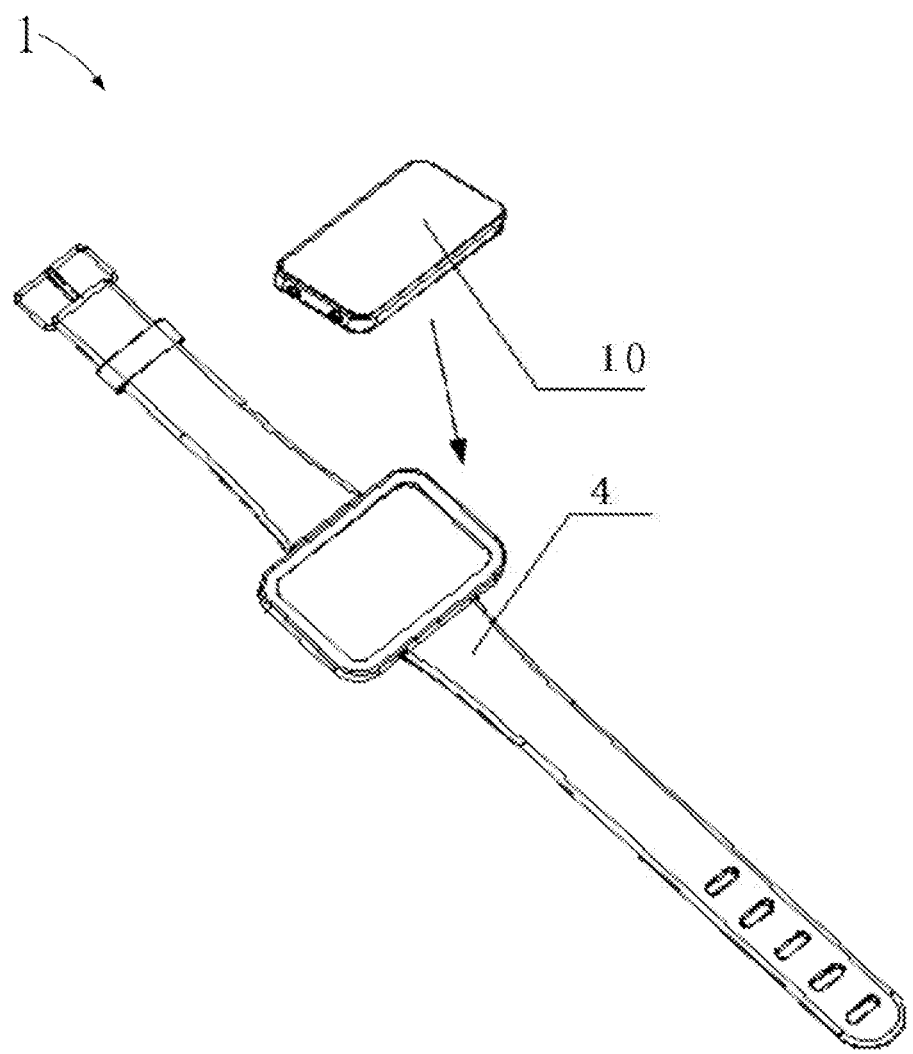
FIG. 17 is a diagram illustrating the device body 10 of the wearable electronic device of FIG. 16 disengaged from the connecting element 4.

FIG. 16 illustrates a fourth embodiment of an electronic cigarette control system 400. The electronic cigarette 2 defines a mounting groove 3 for receiving the device body 10. When the device body 10 is disengaged from the connecting element 4 as shown in FIG. 17, the device body 10 can be mounted in the mounting groove 3.

The first memory 105 stores an identification information of the wearable electronic device 1.

The first controller 102 controls the first communication interface 106 and the second communication interface 203 to establish data connection with each other, and controls the first communication interface 106 to transmit the identification information to the second communication interface 203.

The second memory 201 stores a preset information.

The second controller 205 obtains the identification information from the second communication interface 205, and determines whether the identification information matches the preset information. When the identification information matches the preset information, the electronic cigarette 2 enables the device body 10. When the identification information does not match the preset information, the electronic cigarette 2 disables the device body 10.

When the electronic cigarette 2 enables the device body 10, the electronic cigarette 2 and the device body 10 cooperatively function as a whole device. The user can operate the device body 10 through the electronic cigarette 2, and can also operate the electronic cigarette 2 through the device body 10. When the electronic cigarette 2 disables the device body 10, the electronic cigarette 2 and the device body 10 function separately. The user cannot operate the device body 10 through the electronic cigarette 2, and also cannot operation the electronic cigarette 2 through the device body 10.

In other embodiments, the first memory 105 can be omitted. The identification information can be stored in the third-party device. The wearable electronic device 1 can obtain the identification information from the third-party device through the first communication interface 106.

In other embodiments, the second memory 201 can be omitted. The identification information can be stored in the third-party device. The electronic cigarette 2 can obtain the identification information from the third-party device through the second communication interface 203.

When the device body 10 is disengaged from the connecting element 4 and then mounted in the mounting groove 3 of the electronic cigarette 2, the first controller 102 controls the first communication interface 106 and the second communication interface 203 to establish data connection with each other, and controls the first communication interface 106 to transmit the identification information to the second communication interface 203.

Figure 18:
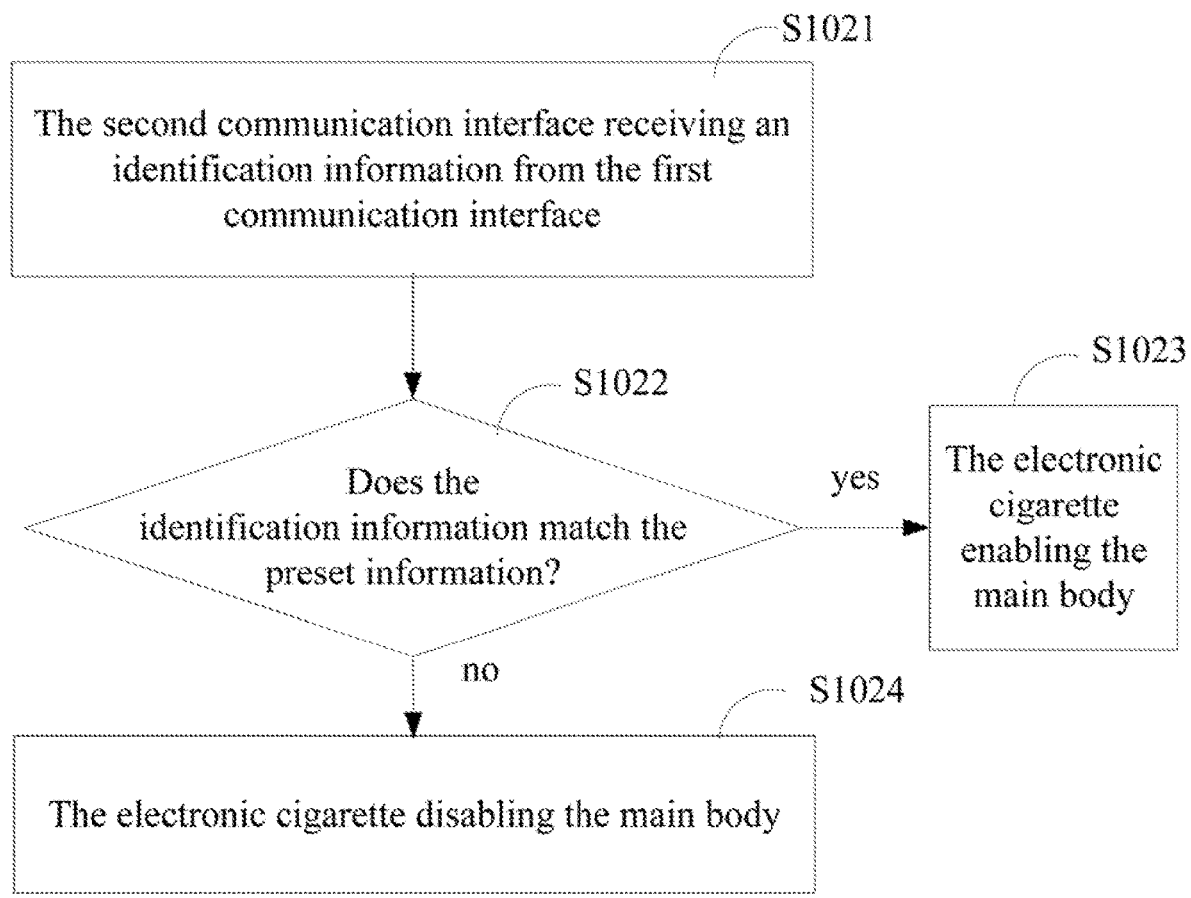
FIG. 18 is a flowchart illustrating a wearable electronic device authorization method executed by the electronic cigarette control system of FIG. 16.

FIG. 18 illustrates a wearable electronic device authorization method executed by the electronic cigarette control system 400. The electronic cigarette authorization method can begin at step S1021.

At step S1021, the second communication interface 203 receives the identification information from the first communication interface 106. Then, the procedure goes to step S1022.

At step S1022, the second controller 205 obtains the identification information from the second communication interface 203, and determines whether the identification information matches the preset information. When the identification information matches the preset information, the procedure goes to step S1023. When the identification information does not match the preset information, the procedure goes to step S1024.

At step S1023, the electronic cigarette 2 enables the device body 10.

At step S1024, the electronic cigarette 2 disables the device body 10.

In an embodiment, when the electronic cigarette 2 enables the device body 10, the first display screen 104 of the device body 10 displays the operation indications and the working information of the electronic cigarette 2. Then, the second display screen 202 of the electronic cigarette 2 can be omitted.

In an embodiment, when the electronic cigarette 2 enables the device body 10, the second power supply 206 can charge the first power supply 103.

In an embodiment, when the electronic cigarette 2 enables the device body 10, the electronic cigarette 2 can obtain the sensed body state data $D_0$ of the user from the device body 10. Then, the electronic cigarette 2 has no need to include a second sensor 210, as illustrated in the second embodiment, to sense the body state data $D_0$ of the user.

In an embodiment, the second communication interface 203 is positioned at the mounting groove 3. When the device body 10 is mounted in the mounting groove 3, one of the first communication interface 106 and the second communication interface 203 is inserted to the other one to achieve wired connection. When the electronic cigarette 2 enables the device body 10, the user can further input a signal for initiating a secret-key mode of the electronic cigarette 2 (hereinafter, "secret-key mode initiating signal") to cause the device body 10 to be a secret key of the electronic cigarette 2. Then, when the device body 10 is separated from the electronic cigarette 2, the first communication interface 106 and the second communication interface 203 are separated to disconnect the wired connection. The electronic cigarette 2 is thereby powered off. The second controller 205 locks out the user input interface 204 to prevent the user input interface 204 from receiving control signals that can control the electronic cigarette 2 to operate. For example, a power-on signal is prevented that can control the electronic cigarette 2 to be powered on. When the device body 10 is again mounted to the electronic cigarette 2, the electronic cigarette 2 is powered on, and the second controller 205 unlocks the user input interface 204. The secret-key mode of the electronic cigarette 2 can prevent unauthorized user of the electronic cigarette 2.

The device body 10 can be connected to the connecting element 4 of the wearable electronic device 1, and can also be mounted to the electronic cigarette 2, which can increase the flexibility during actual use. If the user only wants to bring the wearable electronic device 1 when the user goes out, the user only needs to separate the device body 10 from the mounting groove 3 of the electronic cigarette 2, and connect the device body 10 to the connecting element 4. After a long use, the device body 10 can be again mounted to the electronic cigarette 2, and be charged by the electronic cigarette 2 in case of insufficient battery power. Furthermore, since the device body 10 has all the functions of the wearable electronic device 1, when the device body 10 is mounted to the electronic cigarette 2, the electronic cigarette 2 can enable every function of the device body 10. For example, the device body 10 can display the operation indications and the working information of the electronic cigarette 2, or the sensed body state data $D_0$ of the user.

At least two of the above first to fourth embodiments can be combined according to need.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended single claim is expressed.

What is claimed is:

1. An electronic cigarette comprising:
   a communication interface configured to receive one of a health level of a user and a body state data of the user; and
   a controller, wherein:
   when the communication interface receives the health level, the controller is configured to obtain the health level and determine a first smoking parameter according to the obtained health level and a relationship between health levels and first smoking parameter;
   when the communication interface receives the body state data, the controller is configured to obtain the body state data, determine a health level of the user according to the obtained body state data of the user and a relationship between body state data and health levels, and determine a first smoking parameter according to the determined health level and a relationship between the health levels and first smoking parameters, the body state data comprising at least one of a number of steps taken by the user, a heart rate, a perspiration rate, and a pulse of the user;
   a power supply; and
   a heat generator, wherein the controller is further configured to control electric power supplied to the heat generator by the power supply according to the first smoking parameter, the first smoking parameter comprises at least one of a time for smoking, a duration for smoking, a number of inhalations when smoking, and working temperature/working voltage/working power of the heat generator.

2. The electronic cigarette of claim 1, wherein the electronic cigarette comprises a manual mode and an automatic mode, the electronic cigarette further comprises a user input interface, one of the manual mode and the automatic mode is selected through the user input interface, when the manual mode is selected, second smoking parameter is input through the input interface, and the controller controls the electric power supplied to the heat generator according to one of the first smoking parameter and the second smoking parameter, the second smoking parameter comprises at least one of the time for smoking, the duration for smoking, the number of inhalations when smoking, and the working temperature/working voltage/working power of the heat generator.

3. The electronic cigarette of claim 2, further comprising a memory for storing the relationship between body state data and health levels and the relationship between the health levels and first smoking parameters, wherein the memory is further configured to store an upper threshold and a lower threshold, the second controller is further configured to compare the input second smoking parameter with the upper threshold and the lower threshold when the manual mode is selected, when the input second smoking parameter is greater than or equals to the lower threshold and less than or equals to the upper threshold, the second controller controls the electric power supplied to the heat generator according to the second smoking parameter, and when the input second smoking parameter is less than the lower threshold or greater than the upper threshold, the second controller locks out the heat generator.

4. The electronic cigarette of claim 3, further comprising an aerosol-forming material and a display screen, wherein the aerosol-forming material is tobacco juice comprising a target element, the communication interface is further configured to receive a first concentration of the target element, the display device is configured to display the first concentration of the target element.

5. The electronic cigarette of claim 3, further comprising an aerosol-forming material and a display screen, wherein the aerosol-forming material is tobacco juice which comprises target element, the memory further stores a relationship between health levels and first concentrations of the target element, the controller is further configured to determine a first concentration of the target element according to the relationship between health levels and first concentrations of the target element, the display device is configured to display the first concentration of the target element.

6. The electronic cigarette of claim 5, further comprising a concentration obtaining unit, the concentration obtaining unit is configured to sense a concentration of the target element in the tobacco juice, the controller is further configured to obtain the sensed concentration of the target element from the concentration obtaining unit, compare the sensed concentration of the target element with the first concentration of the target element, and lock out or unlock the heat generator accordingly.

7. The electronic cigarette of claim 3, wherein the memory further stores at least one pattern image, at least one growth-value range, at least one grade, and a growth value relate to an electronic pet; the memory further stores a relationship between at least one growth-value range and at least one grade of the electronic pet, and a relationship between the at least one grade and at least one pattern image of the electronic pet; wherein an original growth value equals to zero, the controller is further configured to determine whether a recommended smoking scheme is executed, and increases the growth value of the electronic pet by 1 when the recommended smoking scheme is executed, the controller is further configured to determine the growth-value range in which the growth value falls in, determine the grade of the electronic pet according to the relationship between the at least one growth-value range and the at least one grade of the electronic pet, and determine a pattern image of the electronic pet according to the relationship between the at least one grade and the at least one pattern image of the electronic pet, the display screen is further configured to display the determined pattern image, wherein executing the recommended smoking scheme means executing the first smoking parameter.

8. The electronic cigarette of claim 2, wherein the electronic cigarette is in data communication with a wearable electronic device, when an anti-loss mode initiating signal is input to the user input interface, the controller is further configured to obtain the anti-loss mode initiating signal from the user input interface, and control the communication interface to periodically transmit an anti-loss signal to the wearable electronic device in response to the anti-loss mode initiating signal.

9. The electronic cigarette of claim 2, wherein the electronic cigarette is in data communicate with a wearable electronic device, the electronic cigarette further comprises a positioner, when an anti-loss mode initiating signal is input to the user input interface, the controller is further configured to obtain the anti-loss mode initiating signal from the user input interface, and control the positioner to periodically sense a position of the electronic cigarette in response to the anti-loss mode initiating signal and transmit the sensed position to a wearable electronic device.

10. The electronic cigarette of claim 9, wherein the communication interface is further configured to receive an identification of a device body of the wearable electronic device from the wearable electronic device, the memory further stores a preset information, the controller is further configured to obtain the identification information from the communication interface, determine whether the identification information matches the preset information, enable the device body when the identification information matches the preset information, and disable the device body when the identification information does not match the preset information.

11. An electronic cigarette control method applied in an electronic cigarette comprising a heat generator and a power supply, the electronic cigarette control method comprising:
  receiving a body state data of a user, the body state data comprising at least one of a number of steps taken by the user, a heart rate, a perspiration rate, and a pulse of the user;
  determining a health level of the user according to the received body state data of the user and a relationship between body state data and health levels;
  determining a first smoking parameter according to the determined health level and a relationship between the health levels and first smoking parameters, the first smoking parameter comprising at least one of a time for smoking, a duration for smoking, a number of inhalations when smoking, and working temperature/working voltage/working power of the heat generator; and
  controlling electric power supplied to the heat generator by the power supply according to the determined first smoking parameter.

12. The electronic cigarette control method of claim 11, wherein the electronic cigarette comprises a manual mode and an automatic mode, after determining the first smoking parameter, the electronic cigarette control method further comprises:
  displaying the determined first smoking parameter;
  controlling the electric power supplied to the heat generator according to the determined first smoking parameter when the automatic mode is selected; and
  receiving a second smoking parameter when the manual mode is selected, and controlling the electric power supplied to the heat generator according to the received second smoking parameter, the second smoking parameter comprising at least one of the time for smoking, the duration for smoking, the number of inhalations when smoking, and the working temperature/working voltage/working power of the heat generator.

13. The electronic cigarette control method of claim 11, wherein the electronic cigarette comprises a manual mode and an automatic mode, before receiving the body state data of the user, the electronic cigarette control method further comprises:
  controlling the electronic cigarette to enter the automatic or the manual mode according to a user input, wherein the body state data of the user is received when the automatic mode is selected, a second smoking parameter is received when the manual mode is selected, and the electric power supplied to the heat generator is controlled according to the received second smoking parameter, the second smoking parameter comprising at least one of the time for smoking, the duration for smoking, the number of inhalations when smoking, and the working temperature/working voltage/working power of the heat generator.

14. The electronic cigarette control method of claim 12, wherein before controlling the electric power supplied to the heat generator according to the received second smoking parameter, the electronic cigarette control method further comprises:
  comparing the second smoking parameter with an upper threshold and a lower threshold;
  controlling electric power supplied to the heat generator according to the second smoking parameter when the second smoking parameter is greater than or equals to the lower threshold and less than or equals to the upper threshold; and
  locking out the heat generator when the second smoking parameter is less than the lower threshold or greater than the upper threshold.

15. The electronic cigarette control method of claim 11, wherein the electronic cigarette further comprises an aerosol-forming material, the aerosol-forming material is tobacco juice comprising a target element; wherein after determining the health level of the user, the electronic cigarette control method further comprises:
  determining a first concentration of the target element according to a relationship between health levels and first concentrations of the target element; and
  displaying the first concentration of the target element.

16. The electronic cigarette control method of claim 15, wherein the target element is nicotine; wherein after determining the first concentration of the target element, the electronic cigarette control method further comprises:
  sensing a concentration of nicotine in the tobacco juice;
  comparing the sensed concentration of nicotine with the determined first concentration; and
  locking out the heat generator when the sensed concentration of nicotine is greater than the determined first concentration.

17. The electronic cigarette control method of claim 11, wherein the electronic cigarette stores at least one pattern image, at least one growth-value range, at least one grade, and a growth value relate to an electronic pet, the method further comprises:
  determining whether a recommended smoking scheme is executed, wherein executing the recommended smoking scheme means executing the first smoking parameter;

increasing the growth value of the electronic pet by 1 when the recommended smoking scheme is executed;

determining the growth-value range in which the growth value falls in;

determining the grade of the electronic pet according to a relationship between at least one growth-value range and at least one grade of the electronic pet;

determining a pattern image of the electronic pet according to a relationship between at least one grade and at least one pattern image of the electronic pet; and displaying the determined pattern image.

18. The electronic cigarette control method of claim 11, further comprising:

receiving an anti-loss mode initiating signal input;

periodically transmitting an anti-loss signal to a wearable electronic device in response to the anti-loss mode initiating signal.

19. The electronic cigarette control method of claim 11, the electronic cigarette further comprises a positioner, the electronic cigarette control method further comprises:

receiving an anti-loss mode initiating signal input by the user;

controlling the positioner to periodically sense a position of the electronic cigarette in response to the anti-loss mode initiating signal; and transmitting the sensed position to a wearable electronic device.

20. An electronic cigarette control method applied in a wearable electronic device, the electronic cigarette control method comprising:

sensing a body state data of a user, the body state data comprising at least one of a number of steps taken by the user, a heart rate, a perspiration rate, and a pulse of the user;

transmitting the sensed body state data of the user to an electronic cigarette, thereby causing the electronic cigarette to determine a first smoking parameter corresponding to determined health level, thereby causing the electronic cigarette to control electric power supplied to heat generator according to the determined first smoking parameter, the first smoking parameter comprises at least one of a time for smoking, a duration for smoking, a number of inhalations when smoking, and working temperature/working voltage/working power of the heat generator.

* * * * *